US008069886B1

(12) United States Patent
Yanke et al.

(10) Patent No.: US 8,069,886 B1
(45) Date of Patent: Dec. 6, 2011

(54) CAPSULE PREPARATION SYSTEM

(75) Inventors: Scott H. Yanke, Dousman, WI (US);
James Chojnacki, Milwaukee, WI (US)

(73) Assignee: Vulcan Lead, Inc., Milwaukee, WI (US)

( * ) Notice: Subject to any disclaimer, the term of this patent is extended or adjusted under 35 U.S.C. 154(b) by 1169 days.

(21) Appl. No.: 11/756,323

(22) Filed: May 31, 2007

Related U.S. Application Data

(60) Provisional application No. 60/810,293, filed on Jun. 2, 2006.

(51) Int. Cl.
*G21F 5/018* (2006.01)
*B65B 29/00* (2006.01)
*B65B 3/04* (2006.01)

(52) U.S. Cl. .......... 141/252; 141/98; 141/258; 141/262; 141/284; 141/370; 604/414

(58) Field of Classification Search .................... 141/98, 141/236–370; 604/414
See application file for complete search history.

(56) References Cited

U.S. PATENT DOCUMENTS

| 3,376,688 | A | | 4/1968 | Takacs et al. |
| 3,893,278 | A | | 7/1975 | Lewis |
| 4,192,361 | A | | 3/1980 | Moser |
| 5,309,959 | A | * | 5/1994 | Shaw et al. .................... 141/130 |
| 5,479,969 | A | * | 1/1996 | Hardie et al. ................. 141/130 |
| 6,554,818 | B2 | | 4/2003 | Weston et al. |
| 7,343,724 | B1 | * | 3/2008 | Williams et al. ................ 53/471 |
| 7,750,328 | B2 | * | 7/2010 | Tartaglia .................... 250/515.1 |
| 2005/0278066 | A1 | * | 12/2005 | Graves et al. ................. 700/239 |

FOREIGN PATENT DOCUMENTS

WO  WO 03/034444  *  4/2003

* cited by examiner

*Primary Examiner* — Gregory Huson
*Assistant Examiner* — Nicolas A Arnett
(74) *Attorney, Agent, or Firm* — Michael Best & Friedrich LLP

(57) ABSTRACT

A capsule preparation system includes a syringe holder for retaining a syringe, the syringe holder configured for operating a plunger of the syringe, a supply vial for storing a volume of radiopharmaceutical, and a capsule holder for capturing a capsule wherein the capsule holder is configured for selectively releasing the capsule from the capsule holder. At least a portion of the syringe holder is movable along a first direction and a second direction to position the syringe relative to the supply vial and the capsule.

25 Claims, 24 Drawing Sheets

CAPSULE PREPARATION SYSTEM

CROSS-REFERENCE TO RELATED APPLICATIONS

This application claims priority from U.S. Provisional Patent Application No. 60/810,293, entitled "Capsule Preparation System", filed Jun. 2, 2006 by Scott H. Yanke and James Chojnacki.

BACKGROUND

The present invention relates to a capsule preparation system, and in particular, an automated system to fill capsules with radiopharmaceuticals.

Radiopharmaceuticals are often delivered to a patient in capsule form. To prepare the delivery capsule, a small quantity of radiopharmaceutical is manually drawn from a vial and injected into a powder pill capsule. The manual process uses small syringes and small quantities of liquid, which must be precisely measured and injected into the capsule. The manual process results in inefficient, expensive and time-consuming preparation of the capsules.

Radiation exposure to personnel preparing capsules from a bulk packaged radiopharmaceutical is high, especially to the hands, when currently available methods and equipment are used. This problem is especially critical with use of high energy radiopharmaceuticals, such as iodine, because of the high energy photons associated with the radionuclides and its extremely short life. With currently available equipment, an operator must draw the dose, remove the syringe from the drawing shield, move the syringe to a dose calibrator, measure the dose in a dose calibrator, replace the syringe in the drawing shield, and then inject the dose into the capsule. Oftentimes, the capsule is injected several times to attain the correct dosage. Repeating this process multiple times using current methods and equipment causes additional radiation exposure to an operator. Adding radiation exposure from these drawing operations to the already high dose received by the operator is dangerous and considered unacceptable. Commercially available equipment for safely preparing radiopharmaceuticals is not available or prohibitively expensive.

SUMMARY

In one embodiment, the invention provides a capsule preparation system including a syringe holder for retaining a syringe, a supply vial for storing a volume of radiopharmaceutical, and a capsule holder for capturing a capsule. The syringe holder is configured for operating a plunger of the syringe, and the capsule holder is configured for selectively releasing the capsule from the capsule holder. At least a portion of the syringe holder is movable along a first direction and a second direction to position the syringe relative to the supply vial and the capsule.

In another embodiment, the invention provides a capsule preparation system for drawing a radiopharmaceutical with a syringe and injecting the radiopharmaceutical into a capsule. The capsule preparation system includes a syringe holder for retaining a syringe, wherein the syringe holder is movable along a first direction and a second direction to position the syringe for drawing a radiopharmaceutical and to position the syringe for injecting drawn radiopharmaceutical into the capsule. The syringe holder includes a dispensing system for operating a plunger of the syringe. The capsule preparation system also includes a vial for storing a volume of radiopharmaceutical, a vial holder for supporting the vial, the vial holder formed of a radiation shielding material and including an opening for allowing access to the vial, and a capsule holder including a pair of grip members for capturing the capsule and configured to selectively release the capsule from the members.

Other aspects of the invention will become apparent by consideration of the detailed description and accompanying drawings.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting.

DETAILED DESCRIPTION

A capsule preparation system provides a radiation-shielded environment for preparing a capsule containing a radiopharmaceutical, i.e., performing a capsule preparation process. A radiation-shielded housing contains the capsule preparation system, which is configured for automated drawing a quantifiable radiopharmaceutical dose from a bulk vial and injecting the dose into the capsule. Examples of the radiopharmaceutical used with the system are iodine-131 or iodine-125, and an example of the capsule is a powder pill capsule, although other known radiopharmaceuticals, liquid solutions, drugs, capsules, and delivery methods may be used.

Figure 1A:
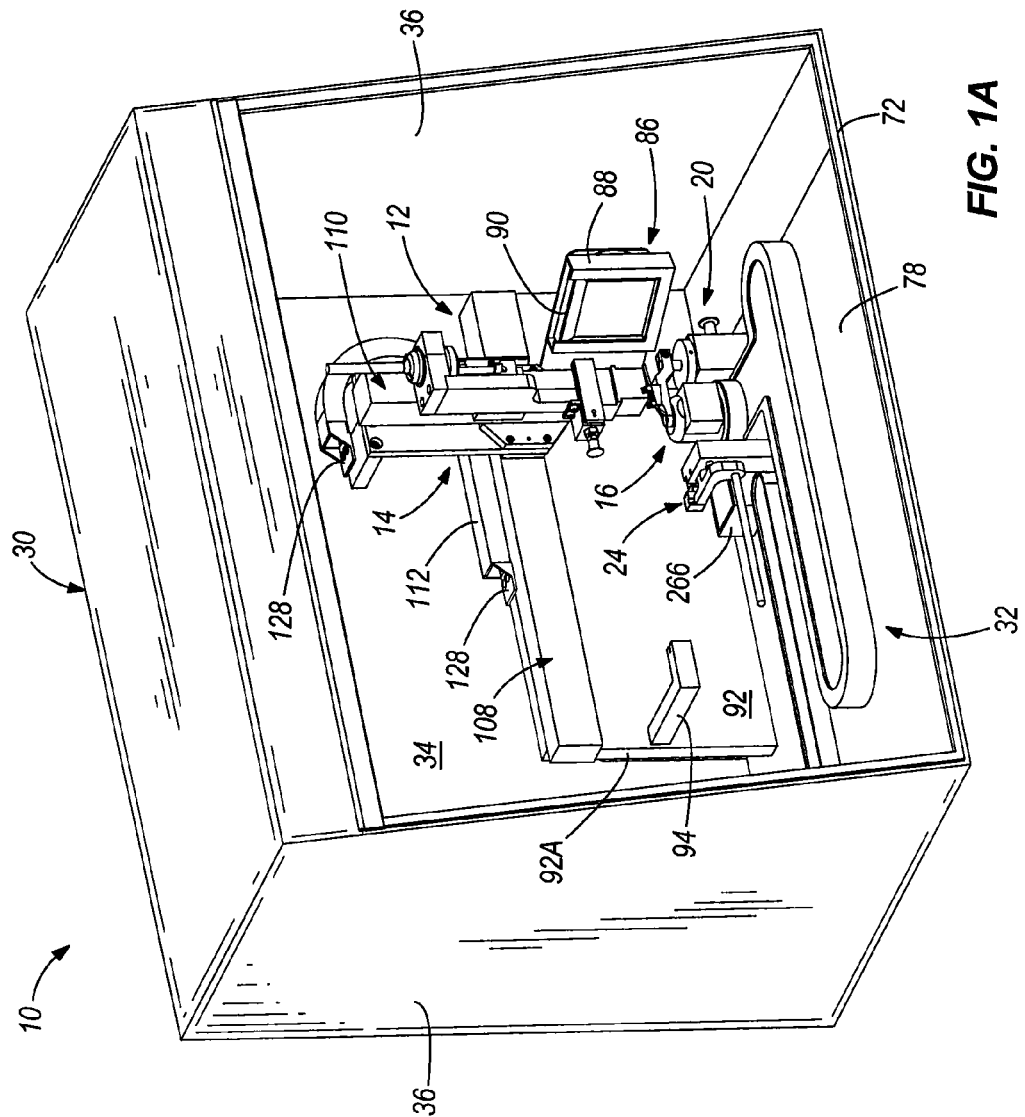
FIG. 1A is a perspective view of a capsule preparation system.
Figure 5:
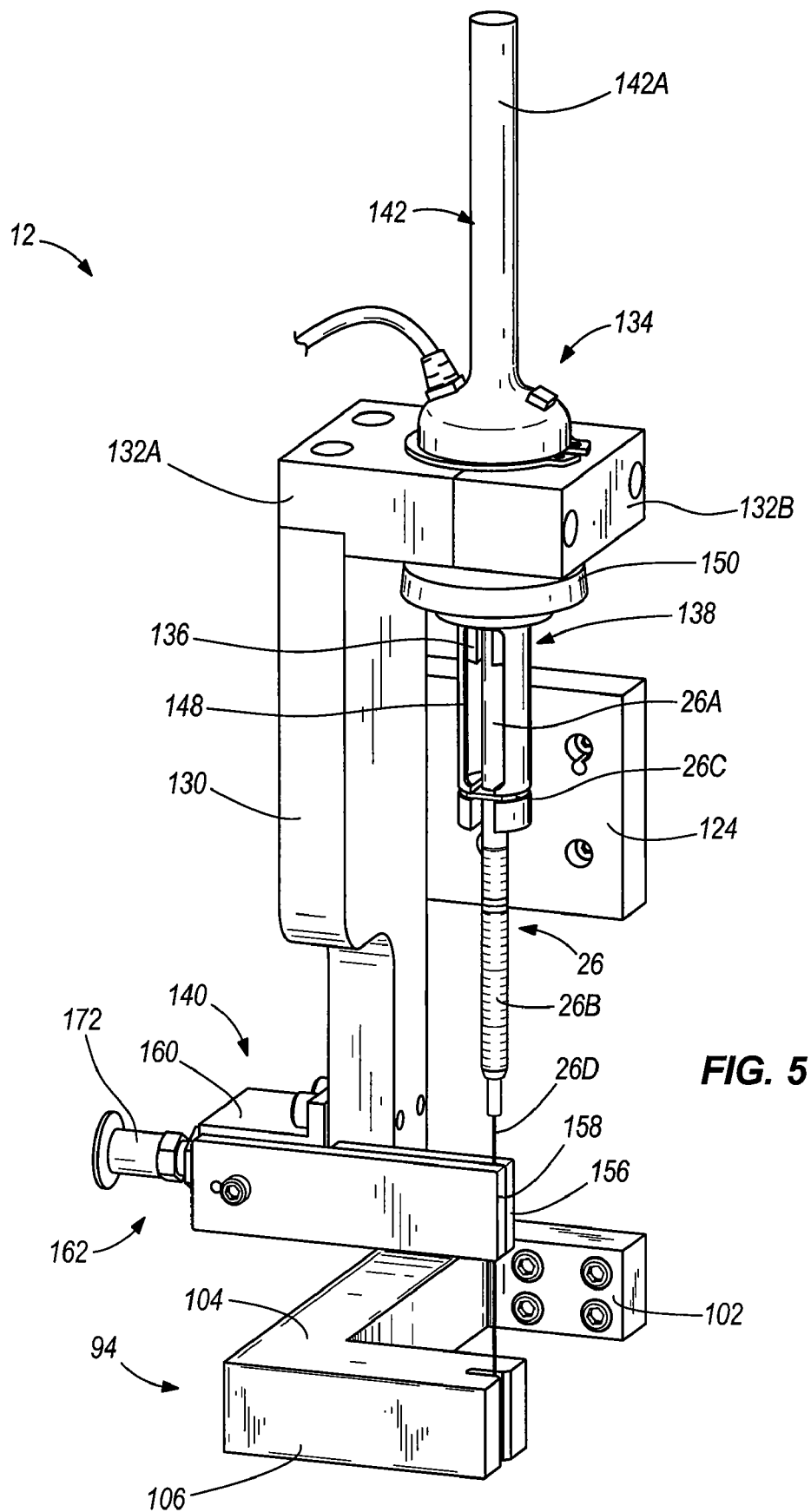
FIG. 5 is a perspective view of the syringe holder system shown in FIG. 4 and supporting a syringe.

FIG. 1A illustrates a capsule preparation system 10 according to one embodiment of the invention. The capsule preparation system 10 includes a syringe holder system 12, a carrier system 14, a vial holder 16, a vial capturing device 20, and a capsule holder 24. The syringe holder system 12 is movable in a first direction and a second direction to move and position a syringe 26 (FIG. 5). In operation, the syringe holder system 12 positions the syringe 26 relative to a vial (not shown) supported by the vial holder 16 and operates the syringe 26 to draw a volume of radiopharmaceutical from the vial. The syringe holder system 12 next positions the filled syringe relative to a capsule 28 (FIG. 16) supported by the capsule holder 24 and operates the syringe 26 to inject the radiopharmaceutical into the capsule 28. The syringe holder system 12 then returns the syringe 26 to its initial position to initiate the preparation process again.

Figure 1B:
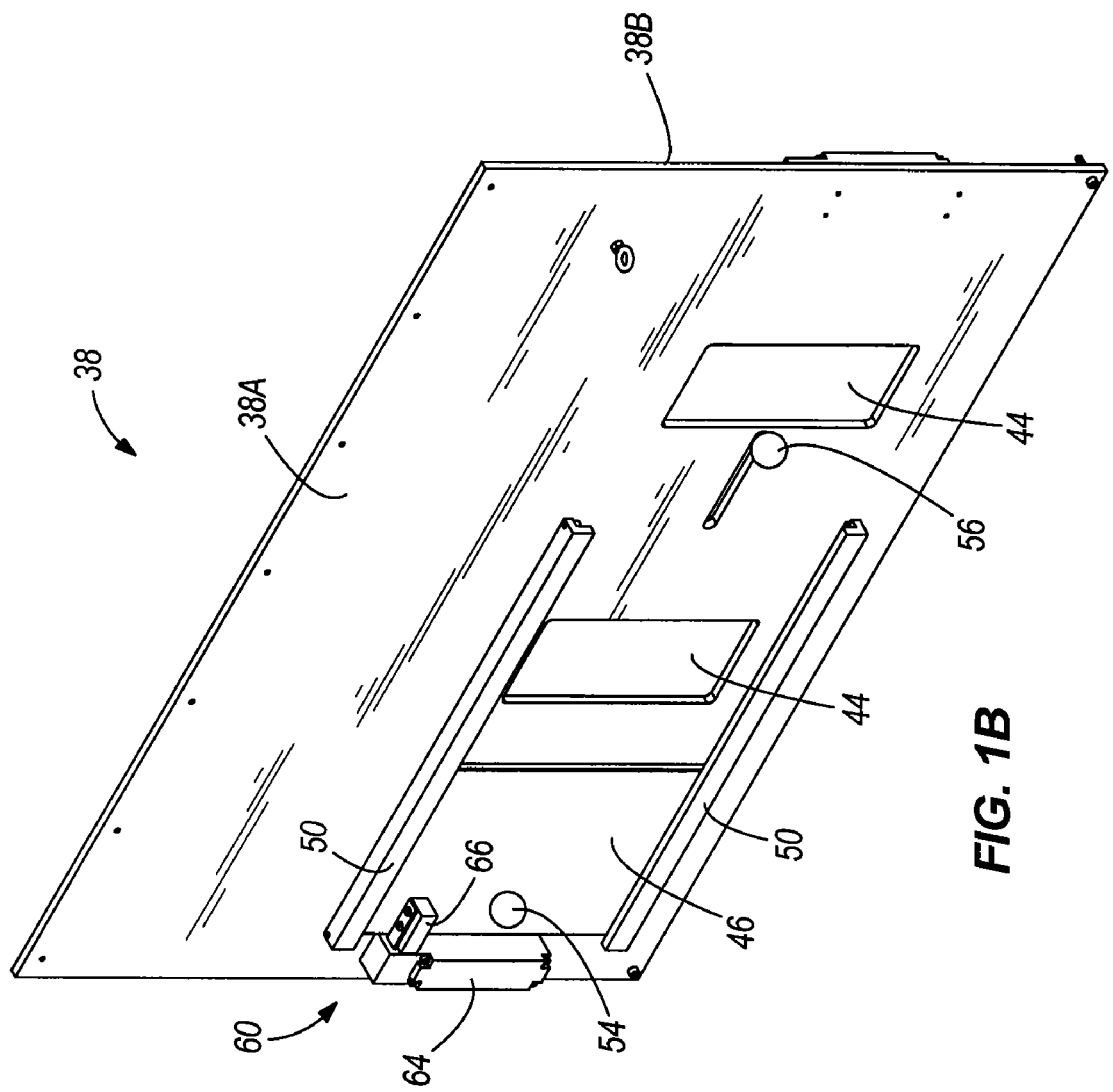
FIGS. 1B-1D illustrate a front panel of the capsule preparation system.
Figure 1C:
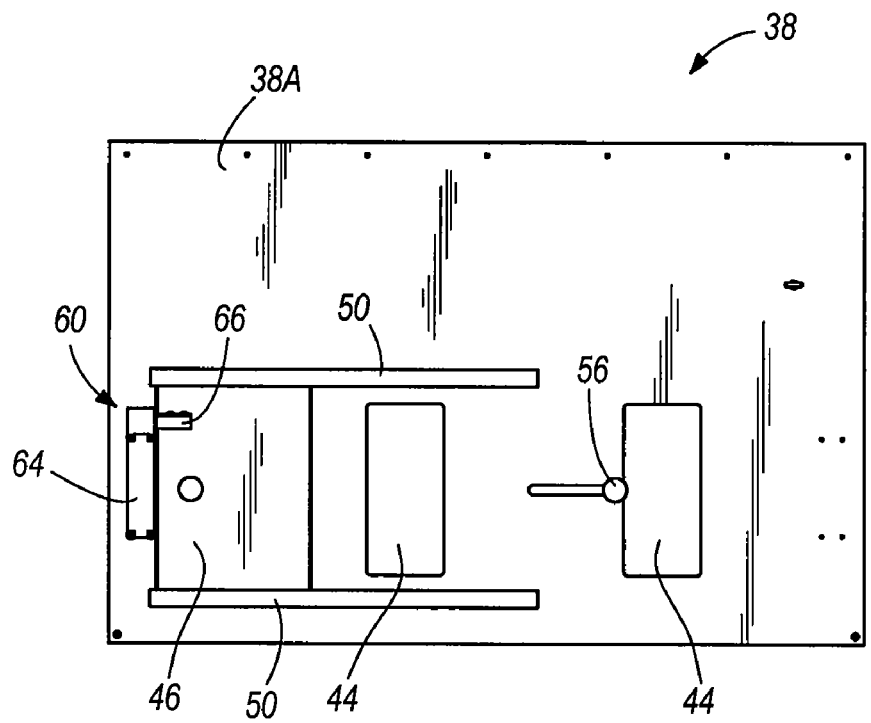
Figure 1D:
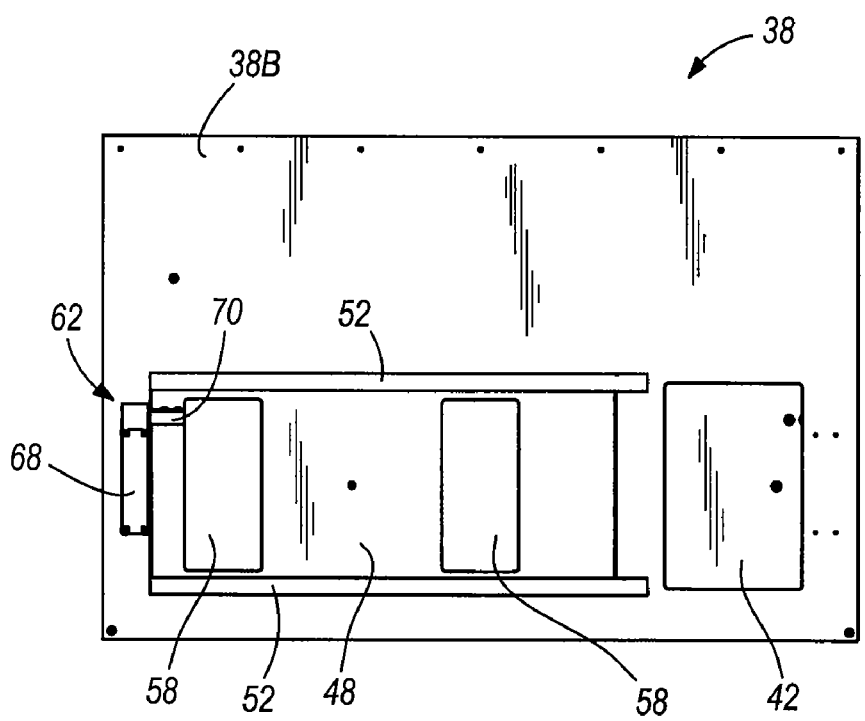
Figure 1E:
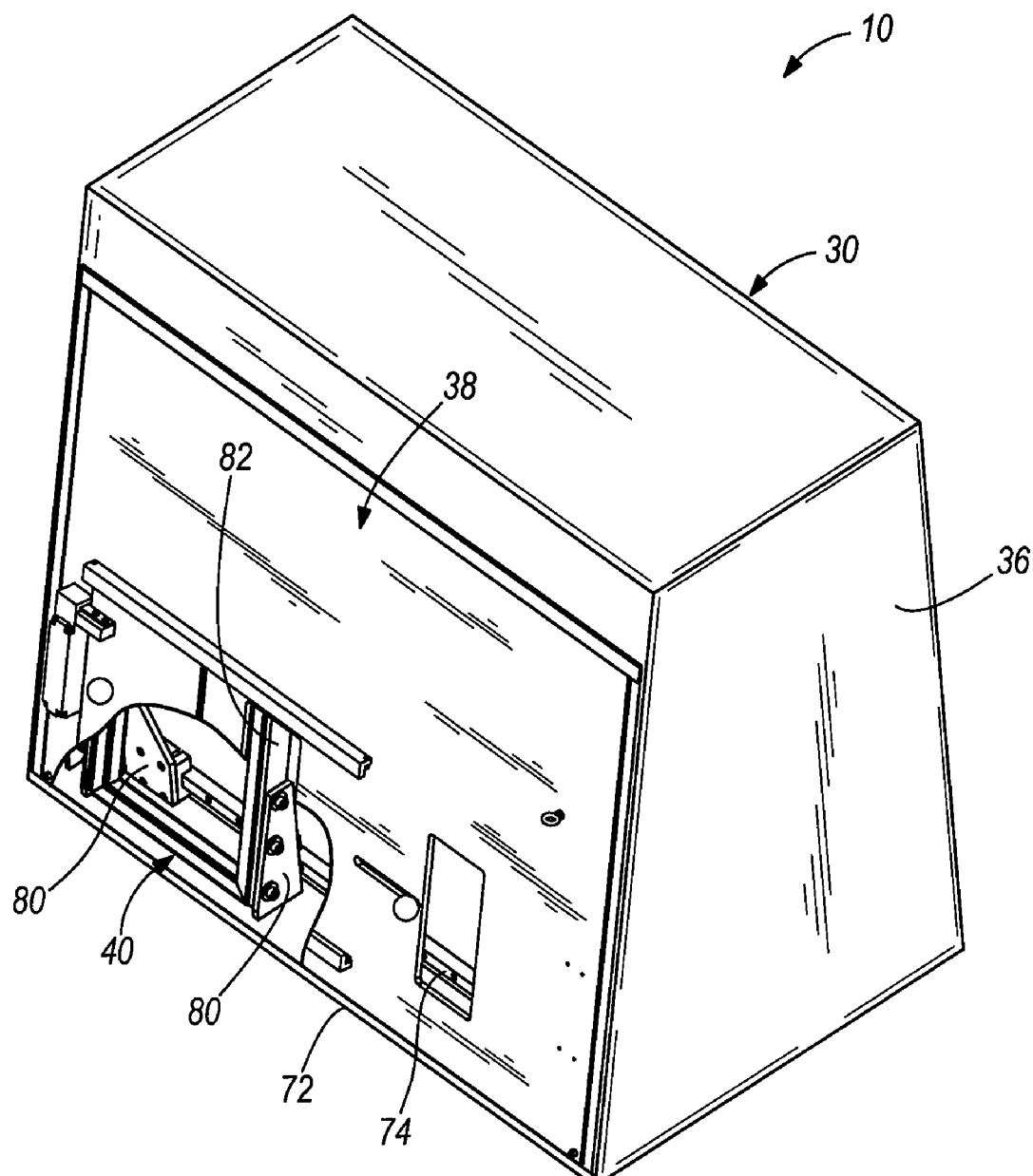
FIGS. 1E-1F illustrate a movable window of the capsule preparation system.
Figure 1F:
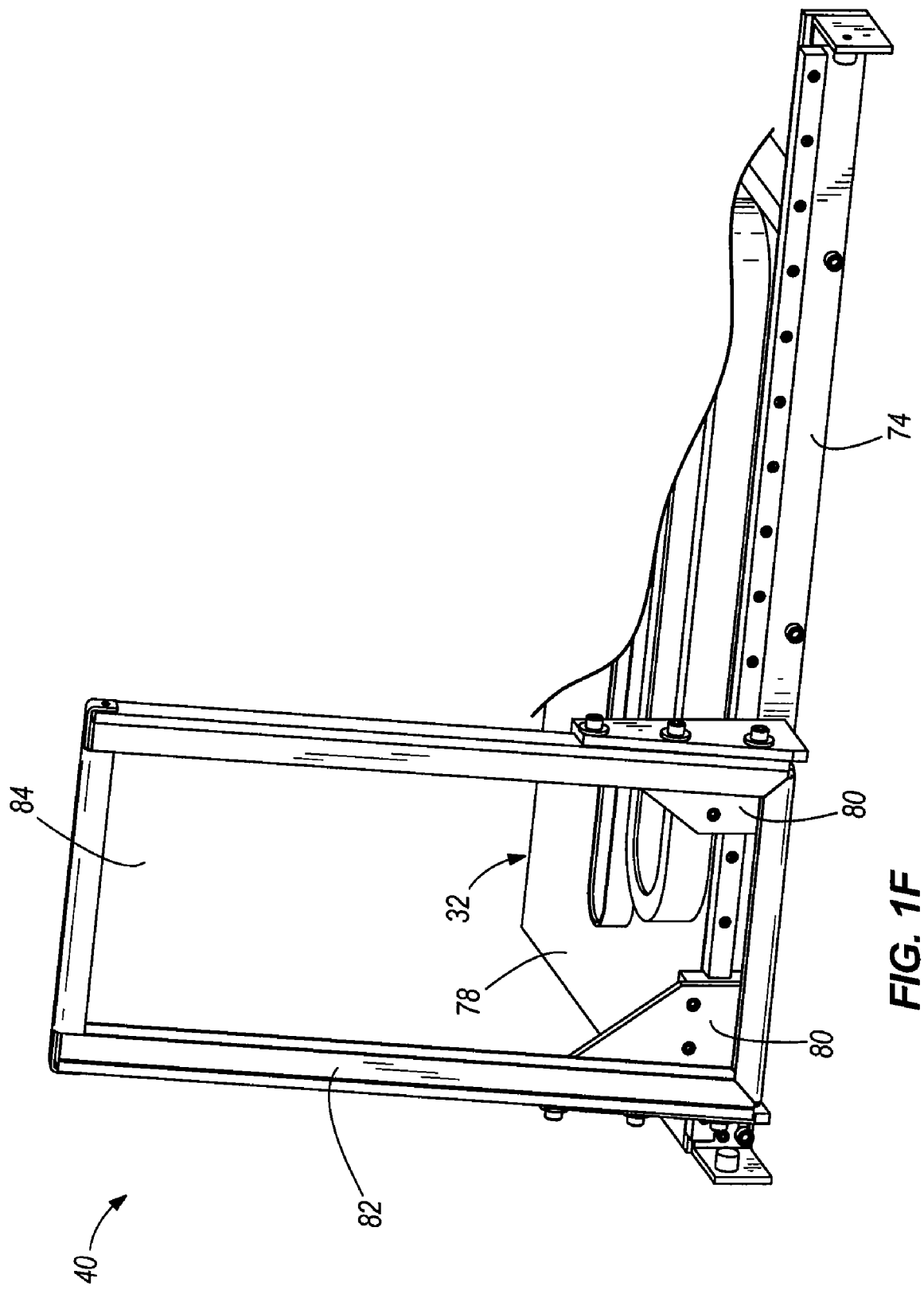

The capsule preparation system 10 is contained within a housing 30, or hood, formed at least in part of radiation-shielding material. In the illustrated embodiment, the housing 30 includes a base plate assembly 32, a rear wall 34, two side walls 36, a front panel 38 (FIGS. 1B-1D), and a sliding window 40 (FIGS. 1E-1F). The front panel 38 and the sliding window 40 are shown removed from the housing 30 in FIG. 1A to show the components within the housing 30. Referring to FIGS. 1B-1D, the front panel 38 includes an exterior surface 38A and an interior surface 38B. The front panel 38 includes three openings for providing access to the capsule preparation system 10, a loading opening 42 (FIG. 1D) and a pair of arm openings 44.

The front panel 38 also includes an exterior sliding door 46, which selectively moves to provide access to the loading opening 42, and an interior sliding door 48, which selectively moves to provide access to the hand openings 44. Each door 46, 48 is supported by a pair of slide rails 50, 52. The exterior door 46 includes a knob 54 for sliding the door 46 back and forth, and the interior door 48 includes a knob 56, accessible from the exterior surface 38A of the panel 38, for sliding the door 48 back and forth. Referring to FIG. 1D, the interior door 48 includes openings 58 that align with arm openings 44 when the door 48 is in an open position. In the illustrated embodiment, the front panel 38 is formed from a plastic material, such as Plexiglas™; however, in a further embodiment, the panel 38 may be formed from a radiation shielding material, such as leaded glass.

FIGS. 1B-1D illustrate the doors 46, 48 in closed positions. Each door 46, 48 includes an interlock system 60, 62 for locking the respective door 46, 48 in a closed position. The interlock system 60 of the exterior door 46 includes an interlock 64 mounted to the exterior surface 38A of the panel 38 and an actuator 66 mounted to the door 46. The interlock system 62 of the interior door 48 includes an interlock 68 mounted to the interior surface 38B of the panel 38 and an actuator 70 mounted to the door 48. In the locked position, the interlocks 64, 68 of the interlock systems 60, 62 engage the actuators 66, 70.

The interlock systems 60, 62 are electrically coupled to and controlled by a controller 285 (FIG. 20) of the capsule preparation system 10. When the doors 46, 48 are in the closed position and the capsule preparation system 10 is in use, the interlock systems 60, 62 are locked to prevent an operator from accessing the interior of the housing 30. Thereby, the doors 46, 48 cannot be opened to gain access to the housing 30. In one embodiment, the capsule preparation system 10 cannot be operated unless the doors 46, 48 are closed. When the capsule preparation system 10 is not in use, the interlock systems 60, 62 are unlocked such that the doors 46, 48 may be opened to provide access to the housing 30. In the illustrated embodiment, the controller 285 of the capsule preparation system 10 operates the interlock systems 60, 62 separately; however, if one door 46, 48 or interlock system 60, 62 is open, the system 10 will not operate. Both doors 46, 48 and interlock systems 60, 62 should be closed to operate the system 10. It should be readily apparent to those of skill in the art that in further embodiments, the interlock systems may operate in unison and a door may be open during operation of the system 10.

As shown in FIG. 1E, the front panel 38 is coupled to the housing 30 at a forward outer edge 72 of the housing 30, for example by fasteners. Positioned within the housing 30 and rearward of the front panel 38 is the sliding window 40. Referring to FIGS. 1E and 1F, the sliding window 40 rides along a track 74 coupled to a forward edge 76 (FIG. 2) of the base 78 of the base plate assembly 32. The track 74 extends a length of the base 78 between the two side walls 36. The sliding window 40 includes a pair of side brackets 80 that ride along the track 74. In the illustrated embodiment, the sliding window 40 includes a frame 82 and window 84 formed of radiation shielding material, such as leaded glass. During use, an operator slides the window 40 along the track 74 to selectively position the window 40 and provide additional radiation shielding for the operator. To move the window 40, an operator must place his or her hands through either of the openings 42, 44 in the front panel 38.

The capsule preparation system 10 also includes a fan module 86 supporting a fan (not shown) for drawing radioactive vapors from the vial (not shown) in the vial holder 16 and out of the capsule preparation system 10. One example of the type of fan used in the capsule preparation system 10 is a muffin fan, although other low-noise fans or blowers may be used, as is known in the art. The fan module 86 includes a fan enclosure 88 for supporting the fan, a filter 90 and a fan back plate (not shown). Vapors pass through the filter 90 before exiting the capsule preparation system 10. In the illustrated embodiment, the fan module 86 is coupled to a support 92 of the base plate assembly 32.

An operator will typically wear gloves formed from radiation shielding material when operating components within the capsule preparation system 10. In an embodiment where the housing includes four walls, the capsule preparation system 10 may include at least one glove box (not shown) for providing access to the interior area of the housing 30 by the operator.

Figure 2:
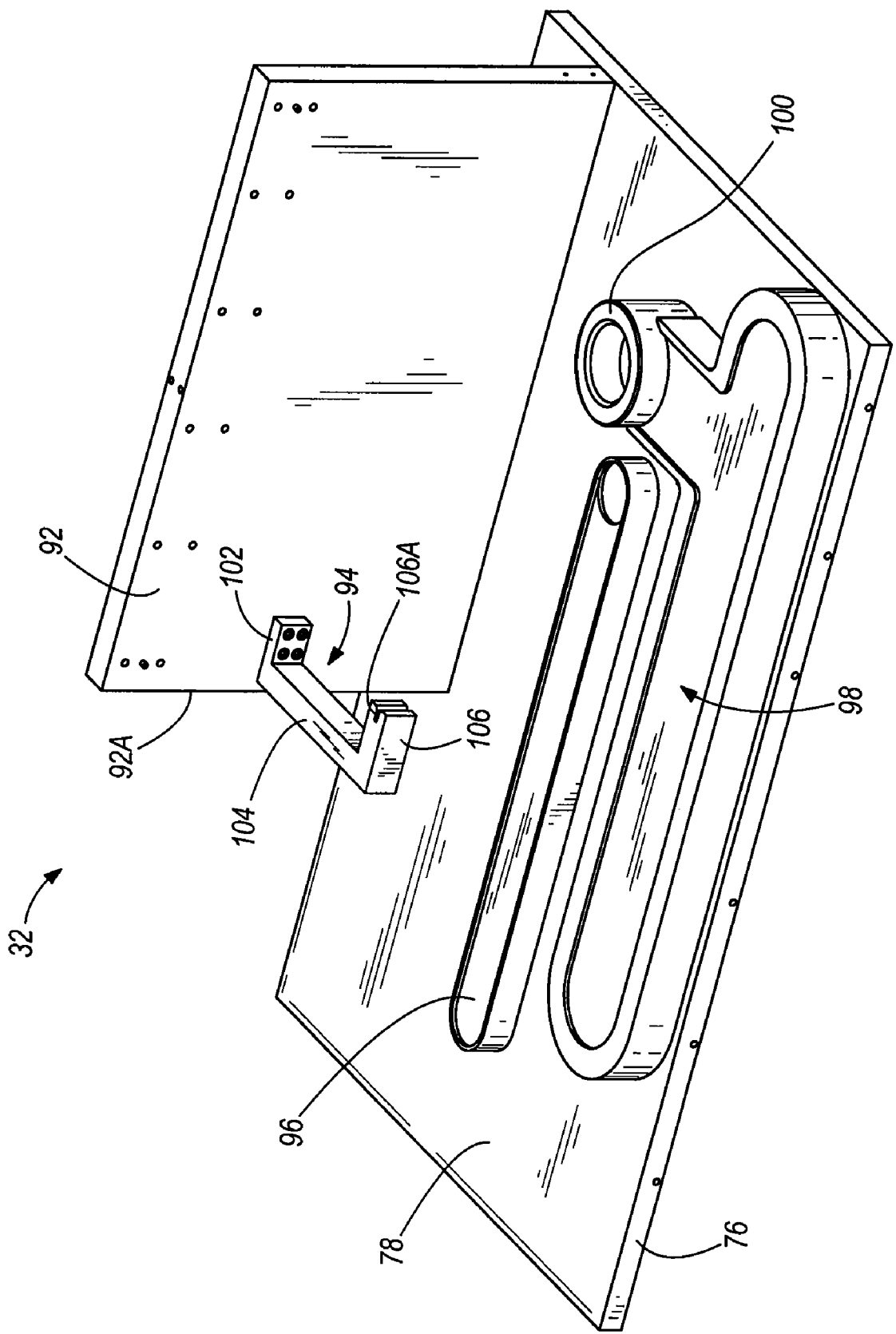
FIG. 2 is a perspective view of a base plate assembly of the capsule preparation system shown in FIG. 1.

FIG. 2 illustrates the base plate assembly 32 of the capsule preparation system 10, which includes the base 78, the support 92, a needle protection shield 94, a first slide 96, a second slide 98, and a support fixture 100. The base 78 supports various components of the capsule preparation system 10, such as the carrier system 14 and the syringe holder system 12, the vial capturing device 20, and the capsule holder 24. In the illustrated embodiment, the support 92 is positioned proximate the rear wall 34 of the housing 32 for supporting the syringe holder system 12.

The needle protection shield 94 is coupled to the support 92 proximate a side edge 92A of the support 92. The needle protection shield 94 includes a coupling portion 102 coupled to the support 92, a central portion 104 that extends outwardly from the support 92 and the coupling portion 102, and a shield portion 106 that extends from the central portion 104. The shield portion 106 includes a slot 106A for housing a syringe needle. When the syringe holder system 12 is in a home position (discussed below), the syringe needle is housed in the slot 106A and shielded by the needle protection shield 94 to prevent an operator from sticking themselves with the needle.

The first slide 96 supports a container (not shown) for transporting filled capsules and provides a surface for sliding the container. The second slide 98 is positioned proximate the support fixture 100, and in some embodiments supports the support fixture 100. The second slide 98 provides a surface for sliding a vial transport container (not shown) to the vial holder 16. The support fixture 100 supports the vial holder 16. In one embodiment, the base 78, the support 92 and the support fixture 100 are formed from aluminum, although other known metals may be used, and the first and second slides 96, 98 of the base plate assembly 32 are formed from plastic.

Figure 3A:
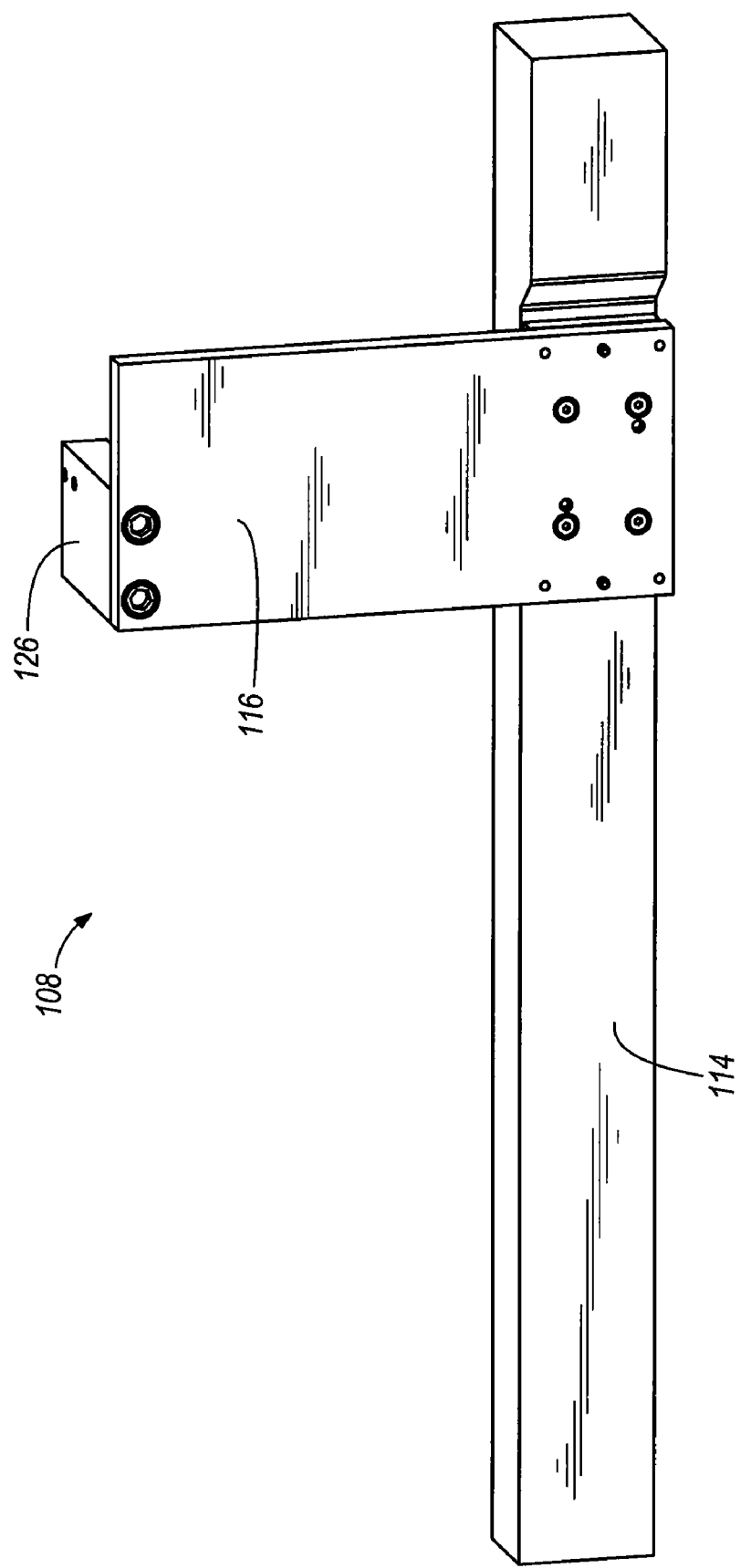
FIG. 3A is a perspective view of a first actuator assembly of a carrier system for the capsule preparation system.
Figure 3B:
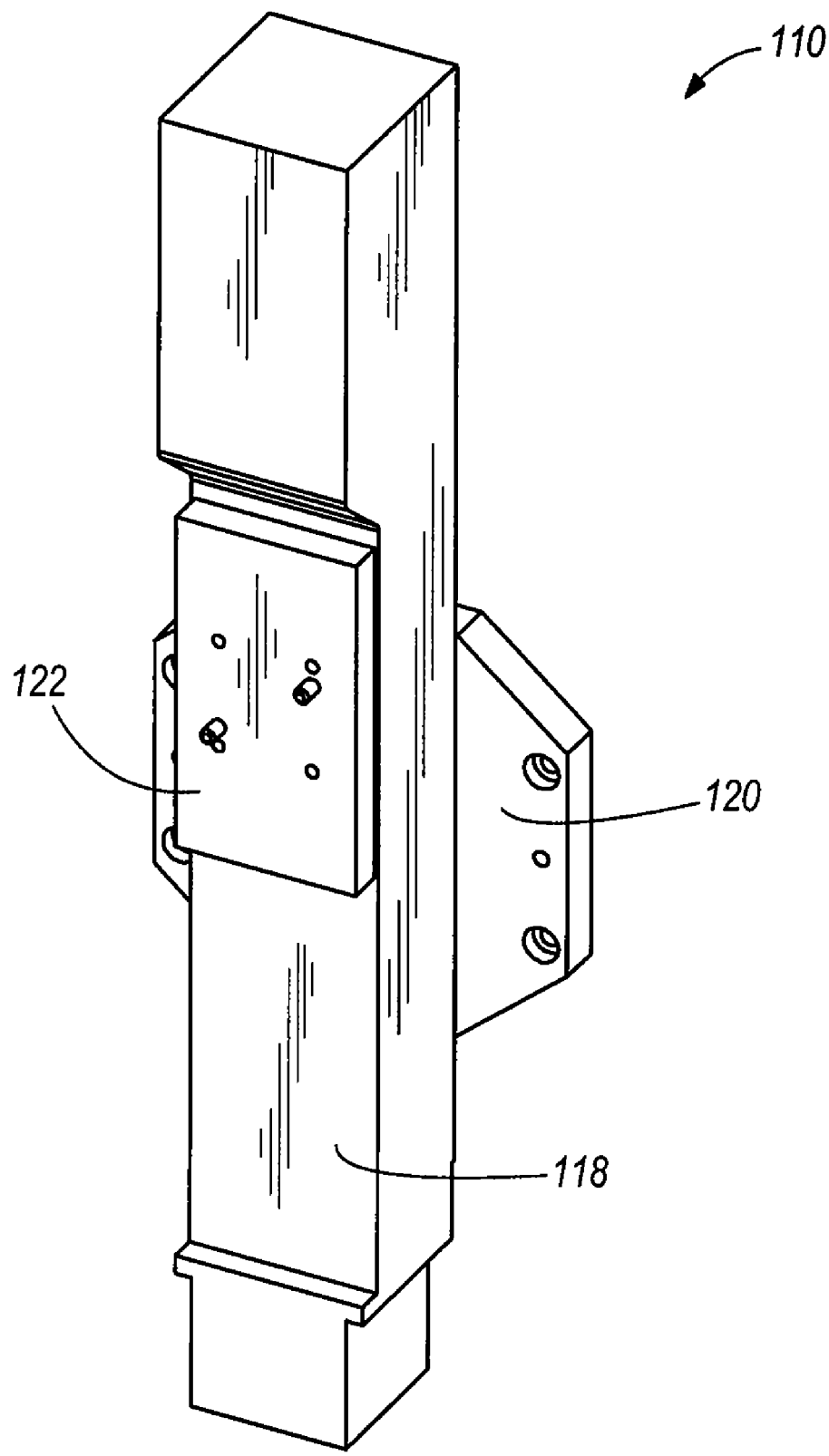
FIG. 3B is a perspective view of a second actuator assembly of the carrier system for the capsule preparation system

Referring to FIGS. 1, 3A and 3B, the syringe holder system 12 is coupled to the carrier system 14 that moves the syringe holder system 12 in a first direction (shown as generally horizontal in FIG. 1) and a second direction (shown as generally vertical in FIG. 1) to move and position the syringe 26. In the illustrated embodiment, the carrier system 14 includes a first actuator assembly 108 mounted horizontally, a second actuator assembly 110 mounted vertically, and a cable carrier 112. The first actuator assembly 108 includes a track 114, or cylinder, coupled to the support 92 of the base plate assembly 32 adjacent an upper edge. An adaptor plate 116 is slidably coupled to the track 114 such that the plate 116 slides back and forth along the track 114 in the first direction.

The second actuator assembly 110 includes a track 118, or cylinder, a first mount plate 120 coupled to a rear surface of the track 118, and a second mount plate 122 slidably coupled to the track 118. The first mount plate 120 is coupled to the adaptor plate 116 of the first actuator assembly 108, for example by screws or other known fasteners, and the syringe holder system 10, via a mounting block 124 (FIG. 4), is coupled to the second mount plate 122, for example by screws or other known fasteners. The second mount plate 122 is slidably coupled to the track 118 such that the second mount plate 122, and thereby the syringe holder system 12, slides back and forth along the track 118 in the second direction. In one embodiment, the tracks 114, 118 and plates 116, 120, 122 of the actuator assemblies 108, 110 are formed from aluminum.

Each actuator assembly 108, 110 includes a servo motor (not shown) for sliding the plates 116, 122 along the respective tracks 114, 118. Movement of the plates 116, 122, and thereby the syringe holder system 12, is controlled by the controller 285 (FIG. 20) based upon preset parameters and user commands to the capsule preparation system 10. The controller 285 commands the actuator assemblies 108, 110 to move the syringe holder system 12 to specific positions within the housing 30. One example of the actuator assemblies 108, 110 used in the capsule preparation system 10 includes the Integrated Combination Series linear actuators by IAI America, Inc. (Torrance, Calif.). The adaptor plate 116 of the first actuator assembly 108 includes a mounting block 124 for attaching a first end of the cable carrier 112, and a second end of the cable carrier 112 is attached to the upper edge of the support 92. Each end of the cable carrier 112 includes a bracket 128 for attaching the cable carrier 112 to the respective block or support. As the syringe holder system 12 moves along the tracks 114, 118, the cable carrier 112 holds the cables of the actuator assemblies 108, 110 together and out of the travel path of the syringe holder system 12.

Figure 4:
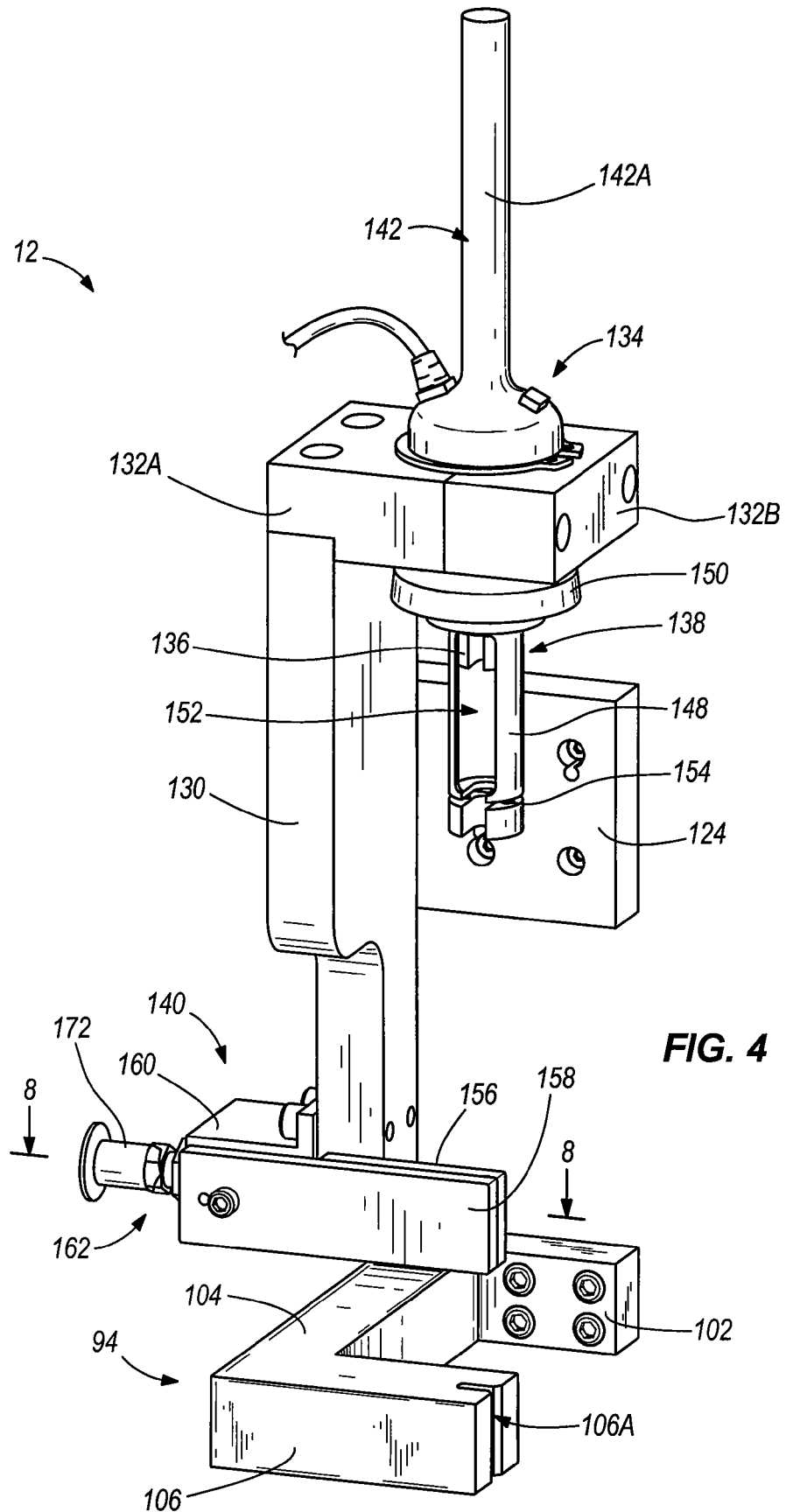
FIG. 4 is a perspective view of a syringe holder system according to one embodiment of the invention.
Figure 6:
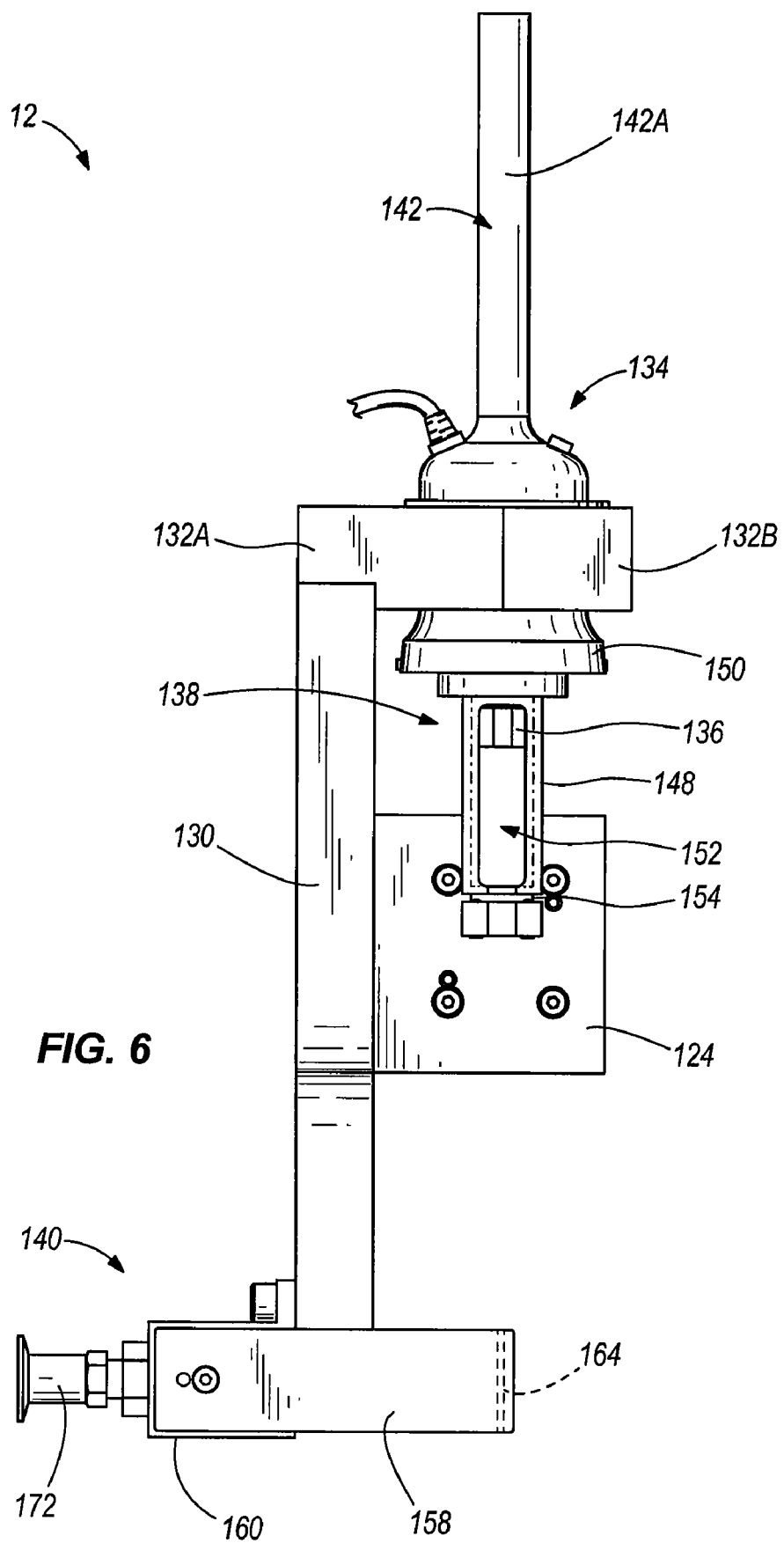
FIG. 6 is a front view of a syringe holder of the syringe holder system.
Figure 7:
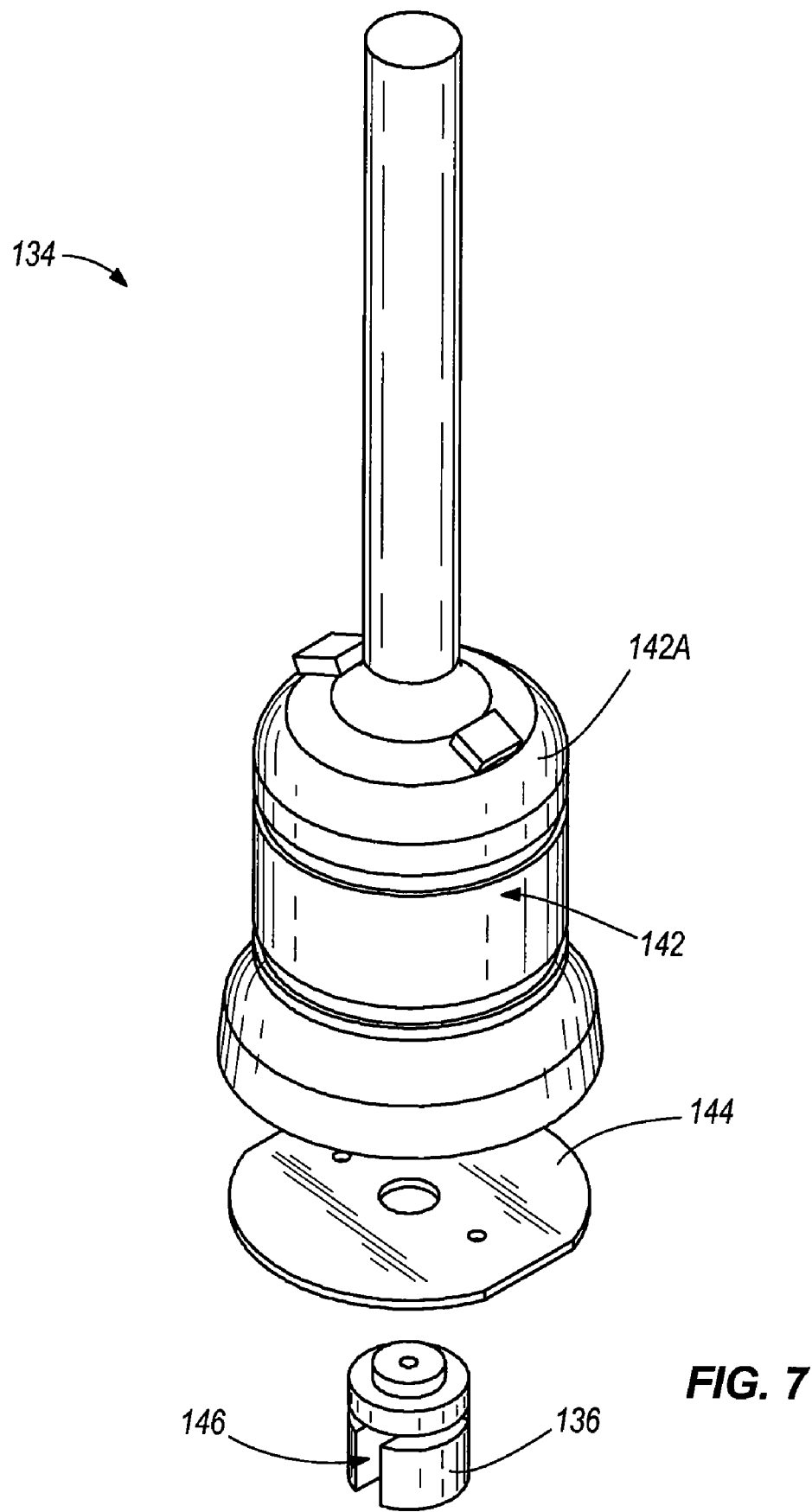
FIG. 7 illustrates a dispensing system and adaptor means of the syringe holder system.

FIGS. 4-6 illustrate the syringe holder system 12 according to one embodiment of the invention, and FIG. 5 shows the syringe 26 supported by the syringe holder system 12. The syringe holder system 12 includes a main plate 130 for supporting the mounting block 124, a pair of support brackets 132A, 132B, a dispensing system 134, an adaptor means 136, a syringe holder 138, and a needle holder 140. The mounting block 124 is coupled to a rear edge of the main plate 130 and is also coupled to the second mount plate 122 of the second actuator assembly 110 to couple the syringe holder system 12 to the carrier system 14. A plurality of fasteners (not shown), such as screws, are used to attach the mounting block 124 to the second mount plate 122, although other known fasteners may be used.

In the illustrated embodiment, the dispensing system 134 is sandwiched between the two support brackets 132A, 132B, which are secured together by a fastener (not shown), and the syringe holder 138 is coupled to the dispensing system 134. One of the brackets 132A, 132B is coupled to an upper end of the main plate 130 such that the dispensing system 134 is supported by the main plate 130. In a further embodiment, another support system may be used to support and couple the dispensing system 134 to the main plate 150, such as an individual plate. The dispensing system 158 includes a stepper motor 142 and a bottom plate 144, and the adaptor means 136 couples the syringe 26 to the motor 142. The adaptor means 136 includes one end for coupling to the dispensing system 134 and a channel 146 for receiving a free end of the syringe plunger 26A. The syringe holder 138 includes a syringe sleeve 148 and a collar 150.

The collar 150 of the syringe holder 138 is coupled to the bottom plate 144 of the dispensing system 134 using fasteners (not shown), as known in the art. The collar 150 includes an opening (not shown) for receiving the adaptor means 136 such that the adaptor means 136 is housed within the sleeve 148 of the syringe holder 138. The syringe sleeve 148 includes a channel 152 and a slot 154, which receives a flange 26C of the syringe 26. Referring to FIG. 5, the syringe 26 includes the plunger 26A, a body 26B, the flange 26C at one end of the syringe body 26B, and a needle 26D attached to an opposite end of the syringe body 26B. The plunger 26A and the syringe body 26B are supported by the syringe holder 138 such that the syringe body 26B and the needle 26D extend downward from syringe holder 138. To support the syringe 26, the flange 26C of the syringe 26 is inserted into the slot 154 of the sleeve 148.

The syringe 26 is coupled to the dispensing system 134 via the adaptor means 136 such that the motor 142 drives the plunger 26A relative to the syringe body 26B to draw or expel a radiopharmaceutical into or out of the syringe 26. The motor 142 provides linear movement of the adaptor means 136, and thereby the syringe plunger 26A captured in the adaptor means 136. The stepper motor 142 includes a housing 142A and a threaded rod (not shown) housed within the housing 142A and the adaptor means 136 is coupled to a free end of the rod (e.g., by threading the adaptor means 136 to the rod). The motor 142 operates to extend and retract the adaptor means 136, and thereby the plunger 26A, relative to the housing 142A. As the motor 142 extends the adaptor means 136, the plunger 26A pushes into the syringe body 26B to dispense fluid from the syringe 26, and as the motor 142 retracts the adaptor means 136, the plunger 26A is pulled from the syringe body 26B to draw fluid into the syringe 26.

One example of the dispensing system 134 used in the capsule preparation system 10 is the AirFree™ dispensing system by Fishman Corporation (Hopkinton, Mass.), which includes a stepper motor. It should be readily apparent to those of skill in the art that other types of motors may be used with the dispensing system 134, such as a servo motor.

The syringe holder 138 supports a plurality of syringes having a variety of sizes and shapes. For example, the syringe holder 138 may support readily available syringes or custom made syringes. In a further embodiment of the invention, the syringe holder 138 defines a syringe body that is coupled to the dispensing system 134. The adaptor means 136 couples the stepper motor of the dispensing system 134 to the syringe plunger 26A, and the motor moves the plunger 26A to draw in or expel radiopharmaceutical from the syringe body 26B.

Also illustrated in FIGS. 4 and 5 is the needle protection shield 94 positioned relative to the syringe holder system 12 below the needle holder 140 when the syringe holder system 12 is in a home position. Referring to FIG. 5, when the syringe 26 is received by the syringe holder 138 and the syringe holder system 12 is in the home position, a free, sharp end of the syringe needle 26D is positioned within the slot 106A of the needle protection shield 94. The needle protection shield 94 prevents an operator from sticking themselves with the needle 26D.

Figure 8:
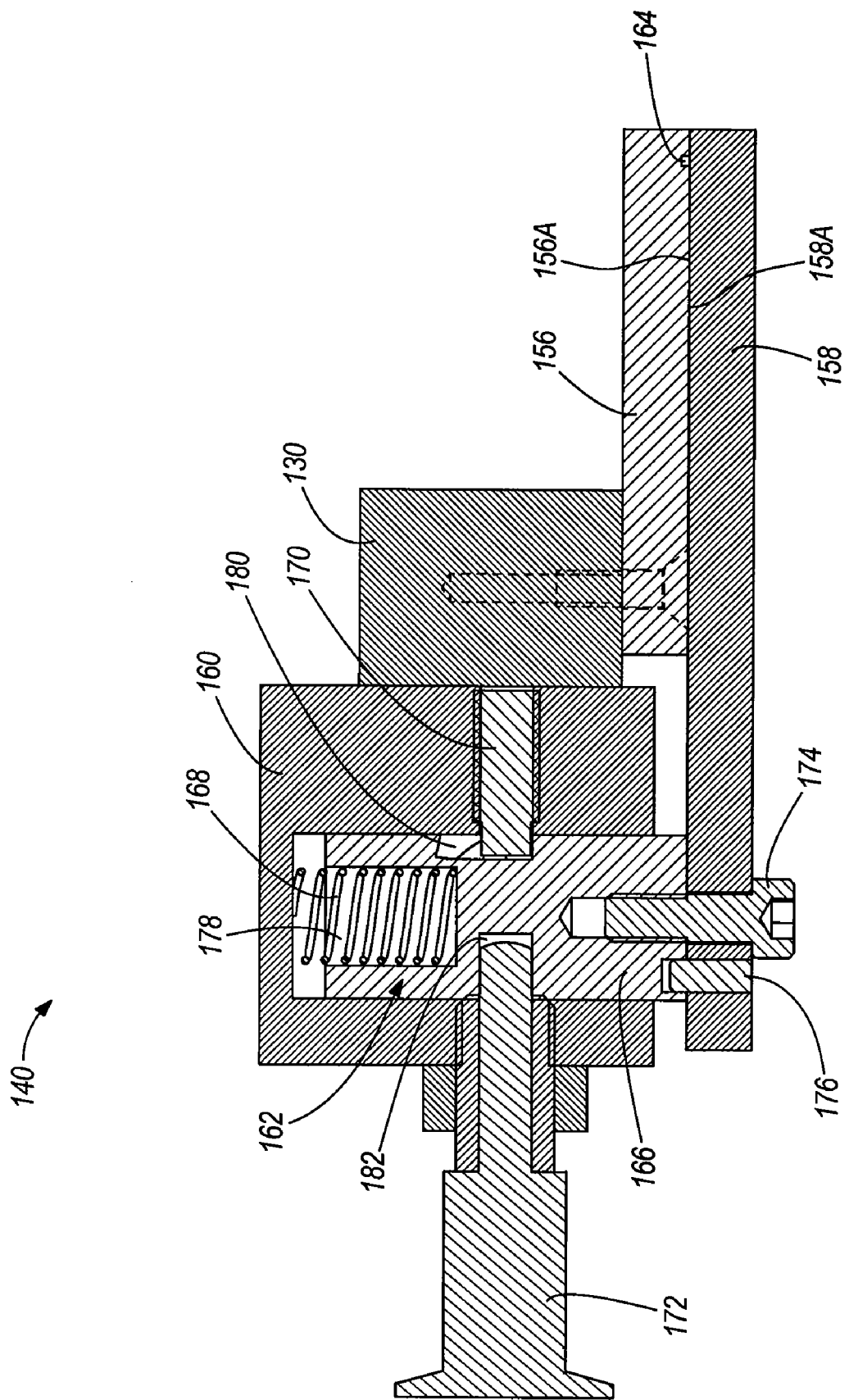
FIG. 8 is a section view of a needle holder of the syringe holder system taken along line 8-8 of FIG. 4.

FIG. 8 illustrates the needle holder 140 for supporting and stabilizing the syringe needle 26D, as well as aligning and guiding the needle 26D relative to the vial holder 16 for repeatability of inserting the needle 26D into the vial. Referring to FIGS. 4-6 and 8, the needle holder 140 is coupled to the main plate 130 of the syringe holder system 12. Because the needle 26D is typically long (e.g., 3.5 inches) and flexible, the needle holder 140 supports and aligns the needle 26D as the syringe holder system 12 moves in the second direction. The needle holder 140 includes a needle mount 156, a needle clamp 158, a housing 160, and an actuation system 162 to move the needle clamp 158 relative to the needle mount 156. The needle mount 202 is coupled to a forward edge of the main plate 130 by a fastener, such as a screw or other known fastener. A free end of the mount 156 includes a groove 164 for receiving the syringe needle 26D. The housing 160 of the needle holder 140 is coupled to a side edge of the main plate 130 by fasteners, such as a screw or other known fastener, such that the needle clamp 158 is positioned adjacent the needle mount 156. When the needle holder 140 is assembled and in a clamp position, engagement surfaces 156A, 158A of the needle mount 156 and the needle clamp 158 are aligned and engaged to retain the syringe needle 26D within the groove 164 of the needle mount 156.

The actuation system 162 of the needle holder 140 moves the needle clamp 158 between the clamp position (shown in FIG. 8) and a release position (not shown). In the clamp position, the needle clamp 158 engages the needle mount 156 such that the needle 26D is supported in the groove 164, and in the release position (not shown), the needle clamp 158 is spaced apart from the needle mount 156 to release the needle 26D. The actuation system 162 includes a slotted shaft 166, a spring 168, a set screw 170, and a knob 172. The needle clamp 158 is coupled to the shaft 166 by a fastener 174, such as a screw or other known fastener, and a pin 176 aligns the clamp 158 with the shaft 166. The shaft 166 includes a bore 178 and the spring 168 is positioned between an inner wall of the housing 160 and the bore 178 of the shaft 166. The spring 168 biases the shaft 166 outward from the housing 160 such that the needle clamp 158 is biased to the release position. The set screw 170 passes through the housing 160 and rides in a helical slot 180 of the shaft 166 and the knob 172 passes through the housing 160 to engage an aperture 182 of the shaft 166 and retain the needle clamp 158 in the clamp position.

In the clamp position, the knob 172 engages the aperture 182 in the shaft 166 to lock the shaft 166 in position within the housing 160. The shaft 166 overcomes the bias of the spring 168 and pulls the needle clamp 158 towards the needle mount 156 such that the two engage to hold the needle 26D within the groove 164. To move the needle clamp 158 to the release position, the knob 172 is pulled outward to disengage with and release the shaft 166. The spring 168 biases the shaft 166 outward from the needle 26D and the set screw 170 rides in the slot 180 as the shaft 166 travels outwardly and rotates relative to the housing 160. The set screw 170 prevents the shaft 166 from traveling completely out of the housing 160. In the release position, the needle clamp 158 is spaced apart from and upward (or downward) from the needle mount 156.

To move the needle clamp 158 back to the clamp position, an operator pushes the clamp 158 towards the needle mount 156. The push force overcomes the bias of the spring 168, which forces the shaft 166 into the housing 160 and against the spring 168. The set screw 170 rides in the slot 180 as the shaft 166 travels inwardly and rotates relative to the housing 160. Once the shaft 166 reaches the innermost position (i.e., the clamp position), the knob 172 drops into the aperture 182 to lock the needle clamp 158 in the clamp position. It should be readily apparent to those of skill in the art that the shaft slot 180 may have other configurations or shapes that facilitate movement of the needle clamp 158 away from the needle mount 152, such as an L-shape, a C-shape, a linear configuration, or curved configuration, or the like.

Figure 9:
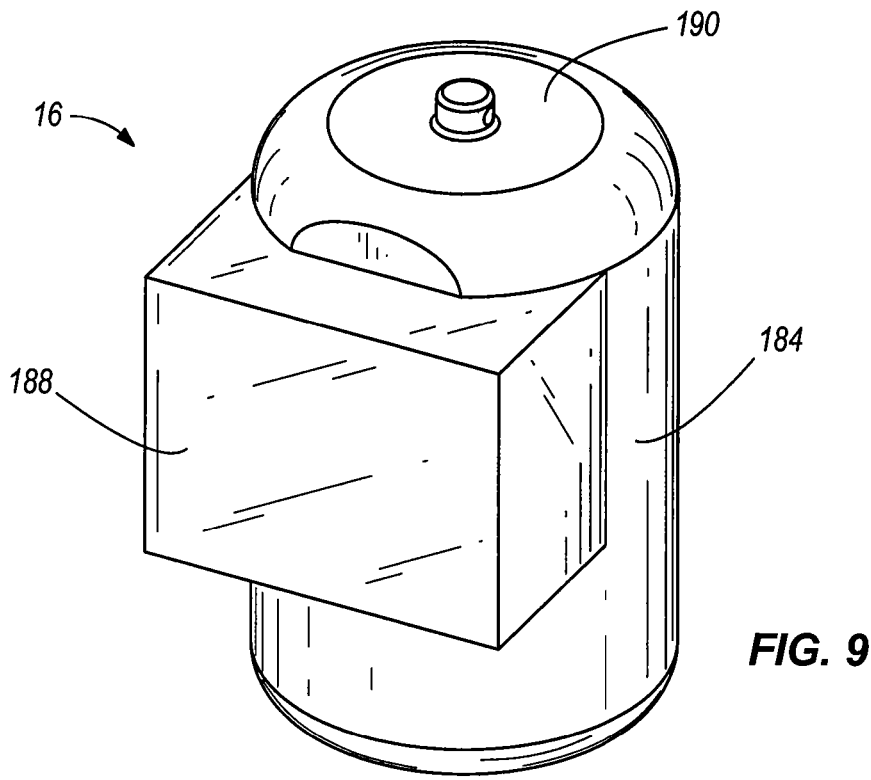
FIG. 9 is a perspective view of a vial holder according to one embodiment of the invention.
Figure 10:
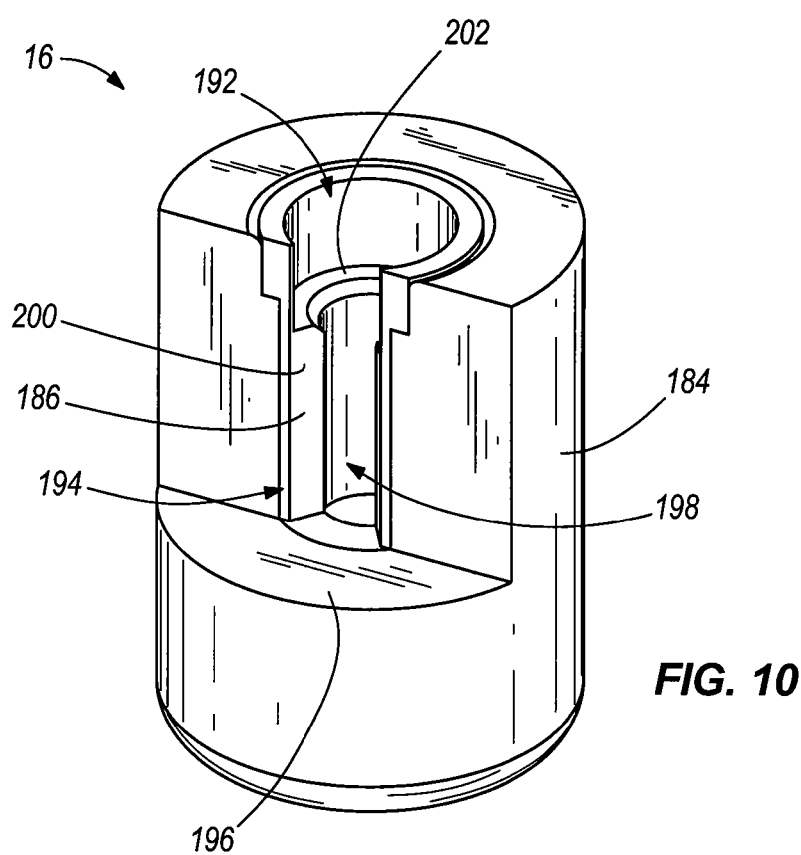
FIG. 10 is a perspective view of the vial holder shown in FIG. 9 with a cover and window removed.

FIGS. 9 and 10 illustrate one embodiment of the vial holder 16 used in the capsule preparation system 10. In the illustrated embodiment, the support fixture 100 of the base plate assembly 32 supports the vial holder 16. The vial holder 16 holds a bulk vial (not shown) containing radiopharmaceutical, although in a further embodiment the vial holder 16 may hold a bulk package, a bulk pack syringe, a unit dose syringe, a unit dose vial, or other radiopharmaceutical supply source. The vial holder 16 includes an outer casing 184, a vial sleeve 186, a window 188 and a cover 190. FIG. 10 illustrates the vial holder 16 with the window 188 and the cover 190 removed.

The outer casing 184 is formed of a radiation shielding material (e.g., lead or a tungsten-impregnated material) and defines a chamber for receiving the vial sleeve 186. Referring to FIG. 10, the outer casing 184 includes a first opening 192 to provide access to the chamber and a side opening 194 where the window 188 is coupled to the casing 184. The casing 184 includes a ledge 196 for supporting the window 188. The generally U-shaped vial sleeve 186 defines a generally cylindrical chamber 198 for receiving the bulk vial (not shown). A portion of the sleeve 186 is open adjacent and positioned adjacent the side opening 194 of the casing 184 such that a user may view the sleeve chamber 198 through the window 188. In one embodiment, the vial sleeve 186 may be removed from the outer casing 184 for cleaning or replacement. The vial sleeve 186 includes a peripheral wall 200 having an outer diameter substantially equal to a diameter of the casing chamber, and a height substantially equal to a height of the casing chamber. A ledge 202 extends radially inward from an inner surface of the wall 200 and is recessed from a top edge of the wall 200. The ledge 202 provides support for the vial capturing device 20, as discussed below.

The window 188 is formed of a radiation shielding material (e.g., leaded glass or leaded acrylic). The window 188 attaches to the outer casing 184 proximate the side opening 194 and is supported by the ledge 196. The window 188 provides visual access to the vial holder 16 such that an operator may determine whether radiopharmaceuticals remain in the vial. The chambers of the casing 184 and the sleeve 186 are further enclosed and defined by the window 188. It should be readily apparent to those of skill in the art that in a further embodiment the vial holder 16 does not include a window. The cover 190 of the vial holder 16 is formed of a radiation shielding material (e.g., lead or a tungsten-impregnated material) and selectively covers the vial holder 16 to enclose the chambers. The cover 190 encloses the chambers during transport of the vial holder 16 and is removed to provide access the chambers for inserting and removing a vial or drawing a dose from a vial.

Figure 11:
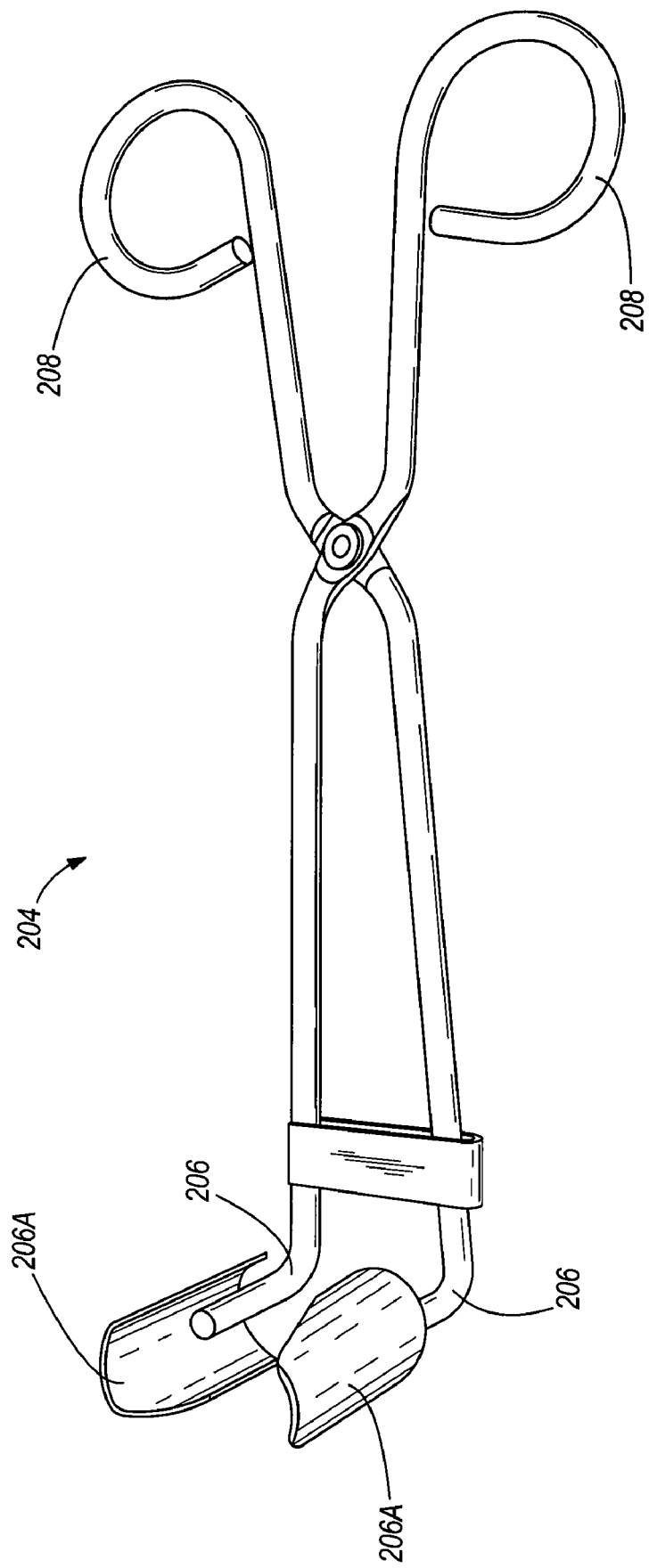
FIG. 11 is a perspective view of one embodiment of a forceps used with the capsule preparation system.
Figure 12:
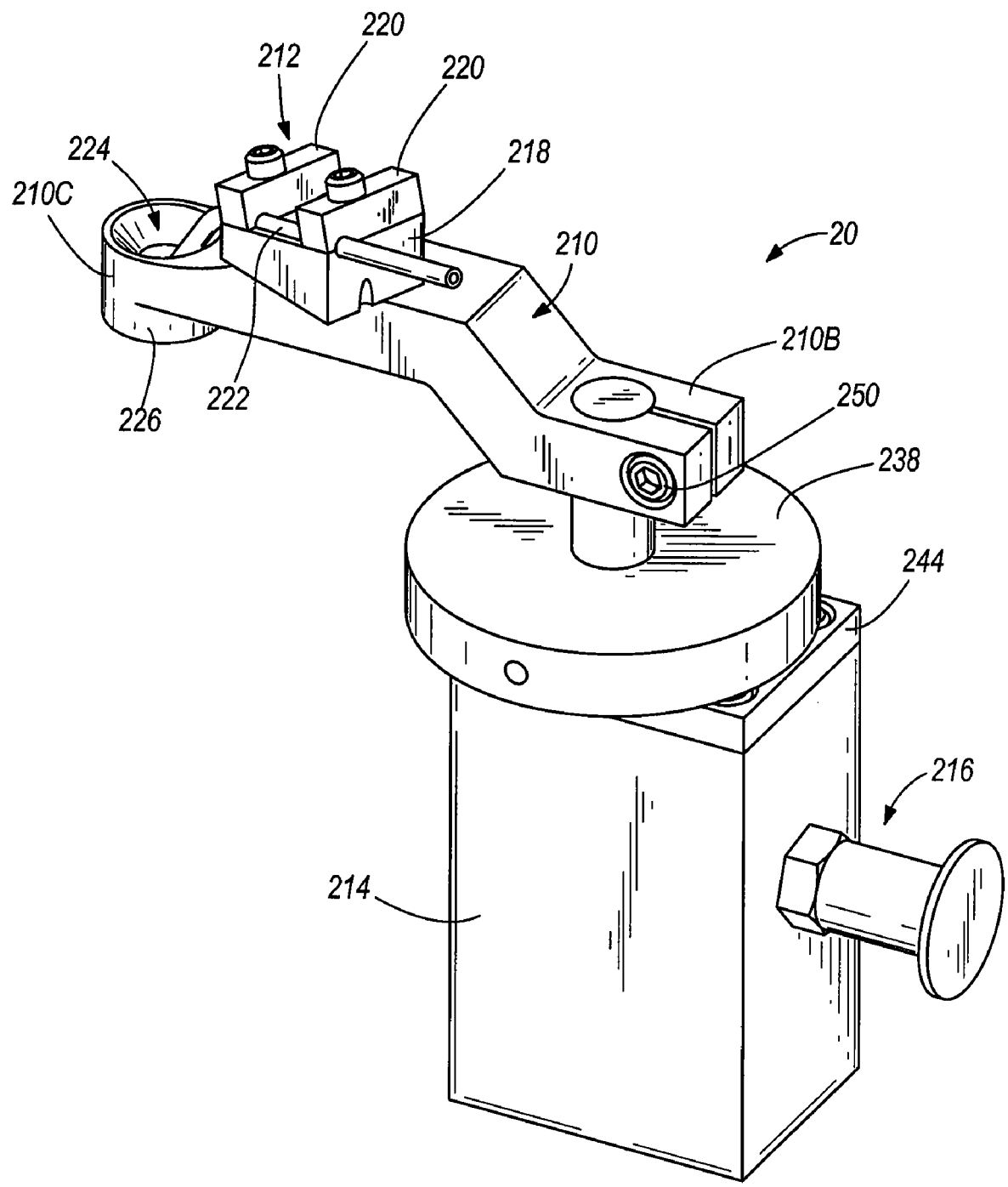
FIG. 12 is a perspective view of a vial capturing device according to one embodiment of the invention.

FIG. 11 illustrates a forceps 204 used for inserting and removing the vial from the vial holder 16. The forceps 204 includes a pair of jaws 206 with handles 208 pivoted together to work in opposition to grasp an object. Each jaw includes a grip member 206A configured for grasping an upper edge of a vial (not shown). The grip member 206A is coupled to a free end of the jaw 206 and extends outwardly from the jaw 206. The grip member 206A has a generally concave shape, or curved surface, that is shaped to complement an outer periphery of a vial. It should be readily apparent to those of skill in the art that the forceps may be used to perform other functions in the capsule preparation system, as described below.

FIGS. 12-13, 14A and 14B illustrate the vial capturing device 20 according to one embodiment of the present invention. The capturing device 20 holds the vial in position within the vial holder 16 while the syringe 26 draws radiopharmaceutical from the vial. Capturing the vial within the vial holder 16 prevents the vial from being lifted when the syringe 26 enters the vial and holds the vial in position. The capturing device 20 includes a guide arm 302 that is movable between a release position (FIG. 14A) and a capture position (FIG. 14B), in which the capturing device 20 holds and centers the vial within the vial holder 16. The capturing device 20 allows repeatability of syringe draws by consistently centering the vial within the holder 16.

Figure 13:
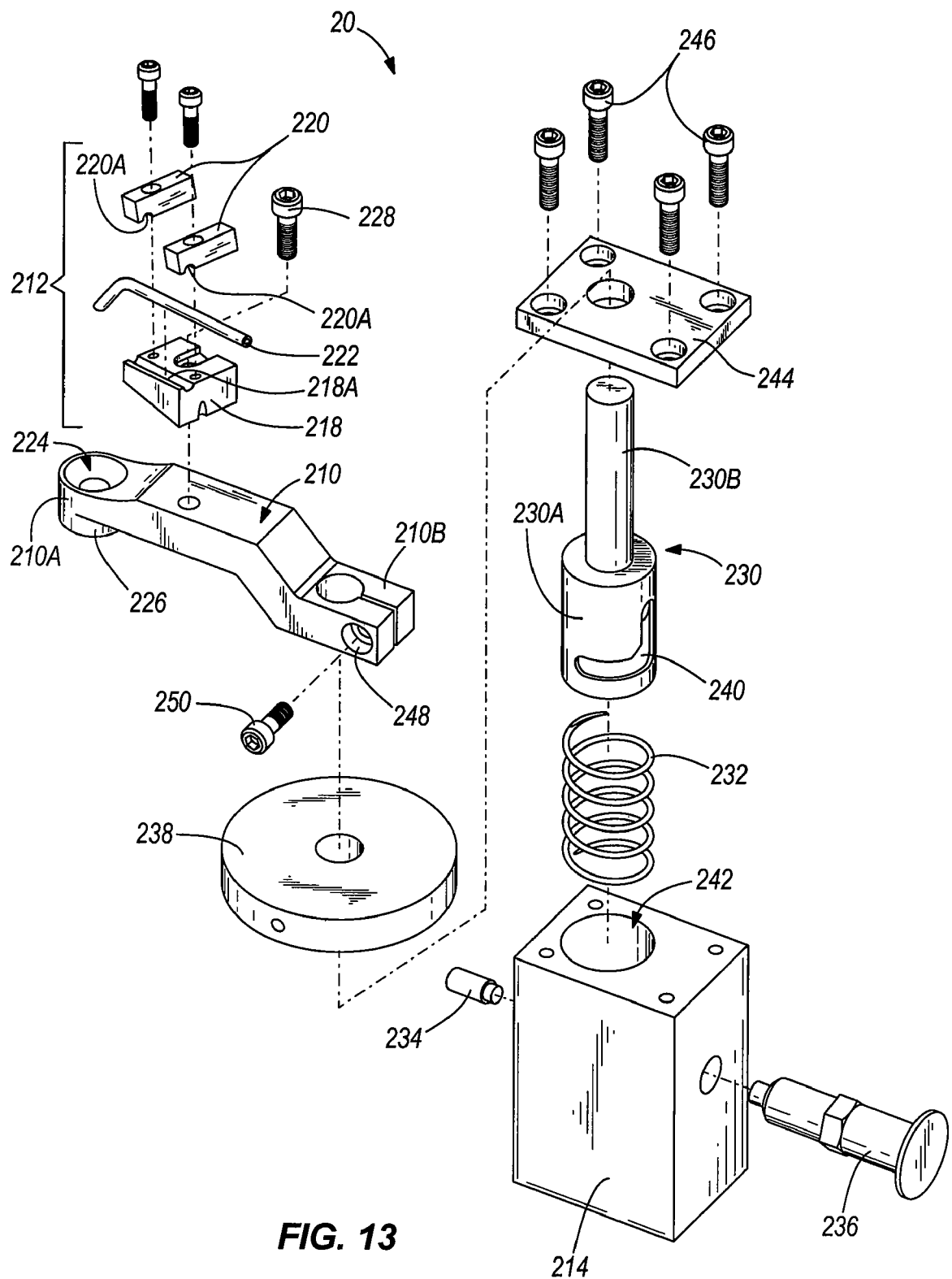
FIG. 13 is an exploded view of the vial capturing device shown in FIG. 12.
Figure 14A:
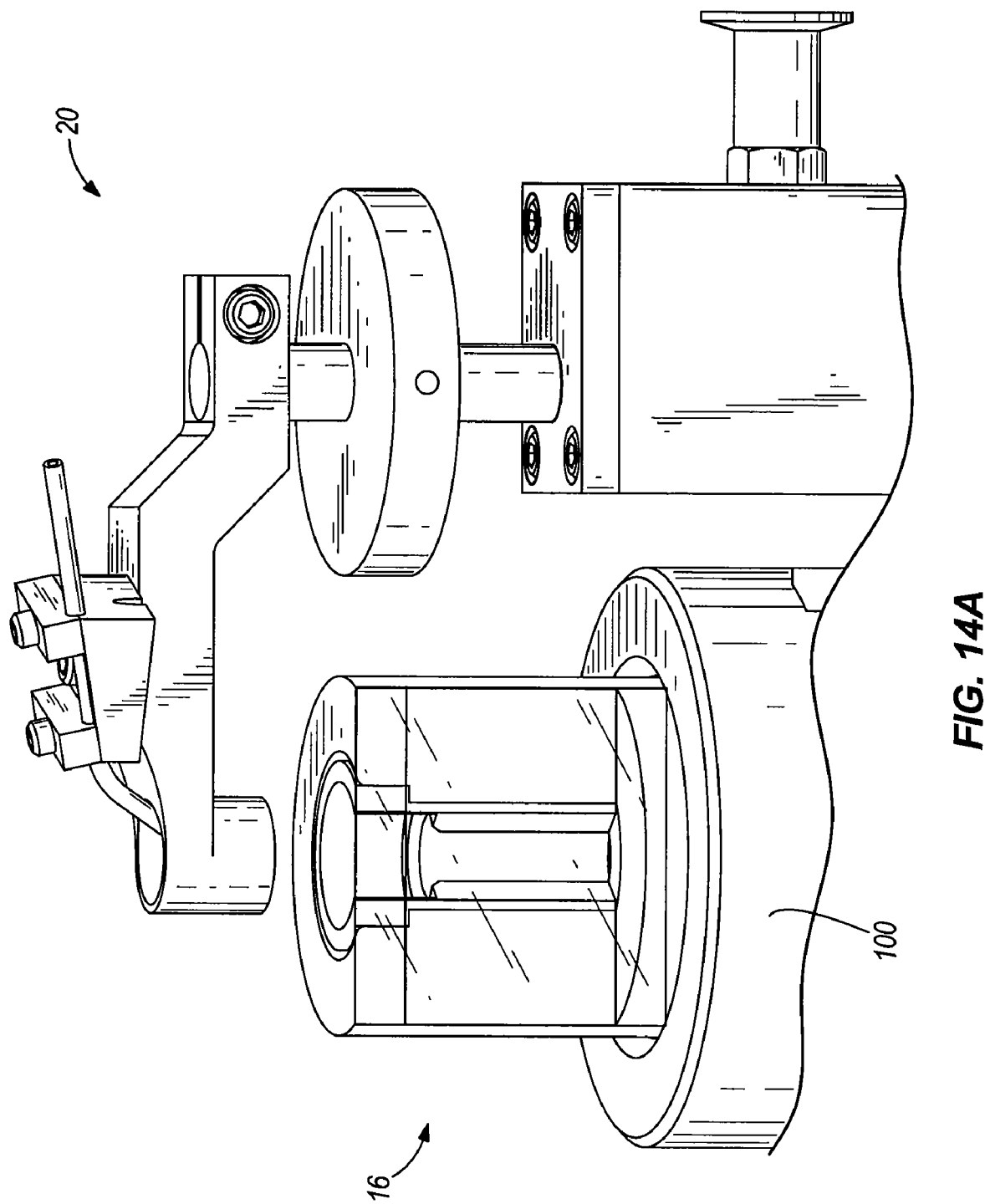
FIG. 14A is a front perspective view of the vial holder and the vial capturing device in a release position.
Figure 14B:
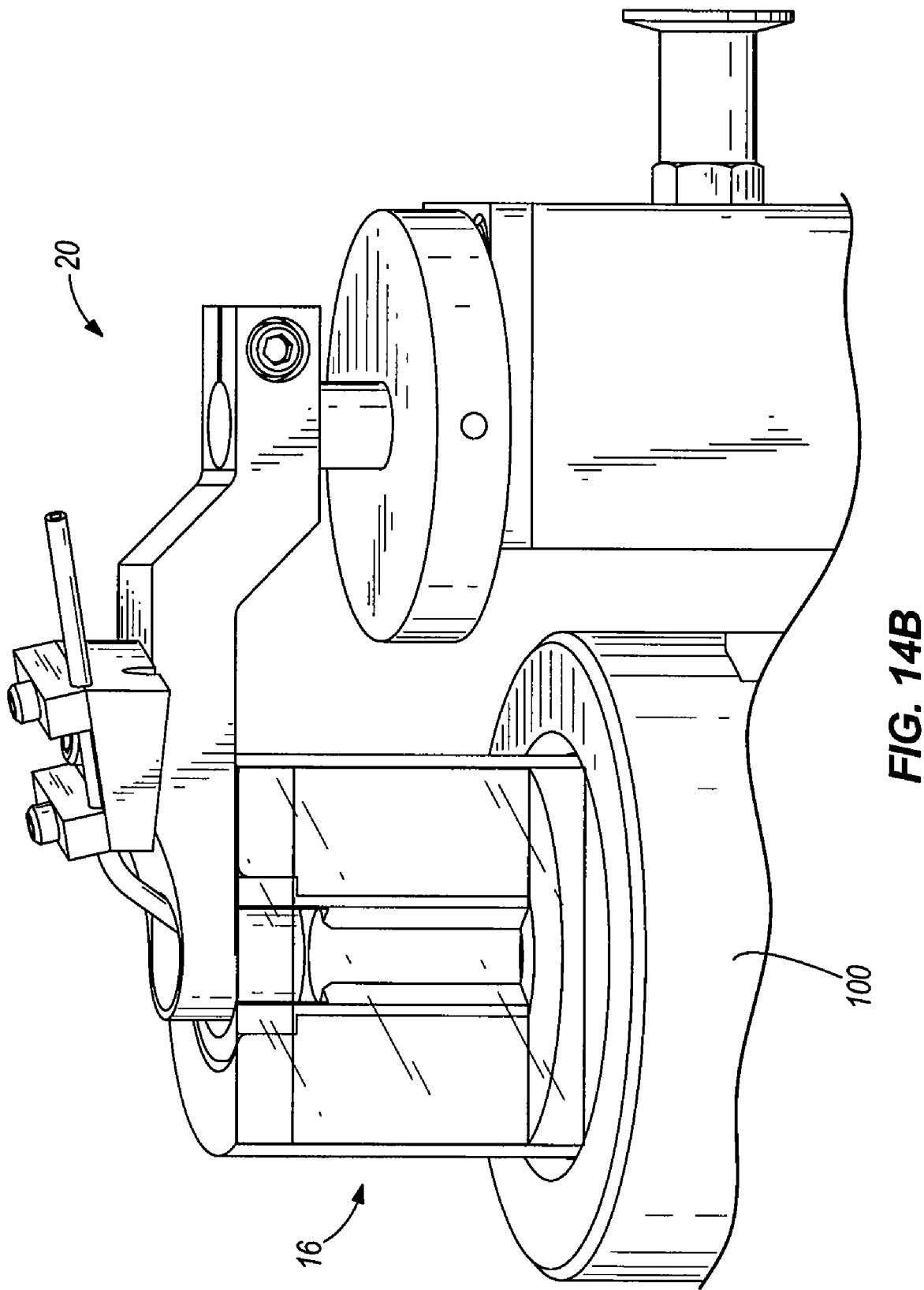
FIG. 14B is a front perspective view of the vial holder and the vial capturing device in a capture position.

The vial capturing device 20 includes a tubing system 212, the guide arm 302, a base 214, and an actuation system 314 (FIG. 13). The tubing system 212 is supported by the needle guide arm 210, and includes a support block 218, brackets 220, and a tube 222 housing a vent needle (not shown). The tube 222 equalizes pressure within the vial and vial holder 16 by directing the tubing system vent needle (not shown) adjacent the vial to draw minute quantities of air out of the vial and into the atmosphere. The vent needle draws radioactive air out so it does not enter the syringe 26, and the tube 222 allows clean air into the vial and guides the vent needle. The tube 222 does not enter the radiopharmaceutical within the vial, and in some embodiments does not enter the vial. The tube 222 is positioned within an opening 330 of the guide arm 302 and allows sufficient room for the syringe needle 26D to pass. In one embodiment, the tube 222 includes a charcoal filter such that radioactive gas does not pass through the tube 222. In another embodiment, both the vent needle and the syringe needle puncture the vial.

A free end 210A of the guide arm 210 defines a capture portion 226 and the tubing system 212 is coupled to the guide arm 210 adjacent the free end 210A. The free end 210A defines the opening 224, through which the tube 222 passes, and the downwardly extending capture portion 226, which captures the vial within the vial holder 16. In the illustrated embodiment, the support block 218 is coupled to the guide arm 210 with a fastener 228, such as a screw or other known fastener. The support block 218 defines a groove 218A for receiving the tube 222 and the brackets 220 are coupled to the support block 218 to hold the tube 222 in position. Each bracket 220 defines a groove 220A whereby the tube 222 is sandwiched between the brackets 220 and the support block 218. Referring the FIG. 12, one end of the tube 222 is positioned within the opening 224 of the capture portion 226, but does not extend beyond the capture portion 226. It should be readily apparent to those of skill in the art that the tube 222 may be coupled to the guide arm 210 using other types of support blocks and brackets, and one end of the tube may extend beyond the capture portion.

The guide arm 210 is rotatably and movably coupled to the base 214 by the actuation system 216. The guide arm 210 rotates relative to and moves horizontally relative to the base 210 to position the capture portion 226 relative to the vial and move the capture portion 226 between the release position and the capture position. In the release position, the capture portion 222 is positioned away from the vial and the vial holder 16. In the capture position, the capture portion 226 is positioned in the vial holder 16 and engages the vial to capture the vial within the vial holder 16.

The actuation system 216 includes a shaft 230, a spring 232, a set screw 234, a knob 336, and a collar 238. The shaft 230 includes a body portion 230A having a generally L-shaped slot 240 and a rod portion 230B. The body portion 230A is positioned within an inner chamber 242 of the base 214 and the rod portion 230B extends out of the base 214 and through a base cover 244 and the collar 238. The spring 232 is positioned between the body portion 230A of the shaft 230 and a closed end of the base 214 to bias the shaft upward with respect to the base 214. The cover 244 retains the shaft 230 within the base 214 and is coupled to the base 214 with fasteners 246. In the illustrated embodiment, the rod portion 230B is coupled to a second end 210B of the guide arm 210. The second end 210B of the guide arm 210 is forked and defines an aperture 248 for receiving the rod portion 230B. A fastener 250, such as a screw or other known fastener, passes through the forked portion of the guide arm 210 to secure the shaft 230 within the aperture 248.

The set screw 234 passes through the base 214 and rides in the shaft slot 240, and the knob 236 passes through the base 214 to engage an aperture (not shown) of the shaft 338 and retain the capturing device 20 in the capture position. The slot 240 defines a travel path of the shaft 230 and the guide arm 210 as the capturing device 20 moves between the release position and the capture position. The knob 236 operates the actuating system 216 to move the capture portion 226 between the release position and the capture position.

In the capture position, the knob 236 engages the aperture in the body portion 230A to lock the shaft 230 in position within the base 214. The shaft 230 overcomes the bias of the spring 232 and holds the capture portion 226 in contact with the vial. To move the guide arm 210 to the release position, the knob 236 is pulled outward to disengage with and release the shaft 230. The spring 232 biases the shaft 230 upward and the set screw 234 rides in the slot 240 as the shaft 230 travels outwardly and rotates relative to the base 214. As the shaft 230 moves upward, the capture portion 226 moves away from the vial and out of the vial holder 16, and the guide arm 210 is rotatable relative to the base 214. The set screw 234 and the cover 244 prevent the shaft 230 from traveling completely out of the base 214.

To move the capture portion 226 back to the capture position, an operator rotates the guide arm 210 and pushes the capture portion 226 into contact with the vial. The push force overcomes the bias of the spring 232, which forces the shaft 230 into the base 214 and against the spring 232. The set screw 234 rides in the slot 240 as the shaft 230 travels inwardly and rotates relative to the base 214. Once the shaft 230 reaches the innermost position (i.e., the capture position), the knob 236 drops into the aperture to lock the guide arm 210 in the capture position. It should be readily apparent to those of skill in the art that the shaft slot 240 may have other configurations or shapes that facilitate movement of the capture portion, such as a helical shape, a C-shape, a linear configuration, or curved configuration, or the like.

Figure 15:
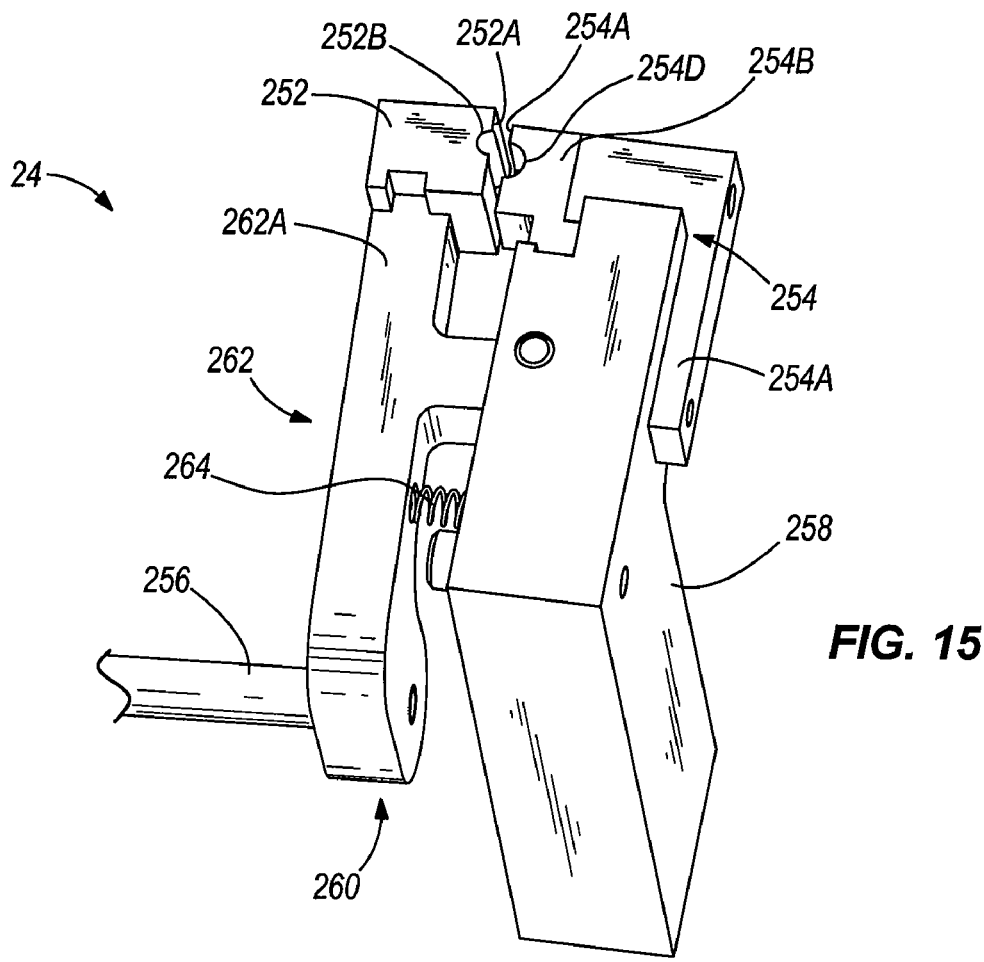
FIG. 15 is a perspective view of a capsule holder according to one embodiment of the invention.
Figure 16:
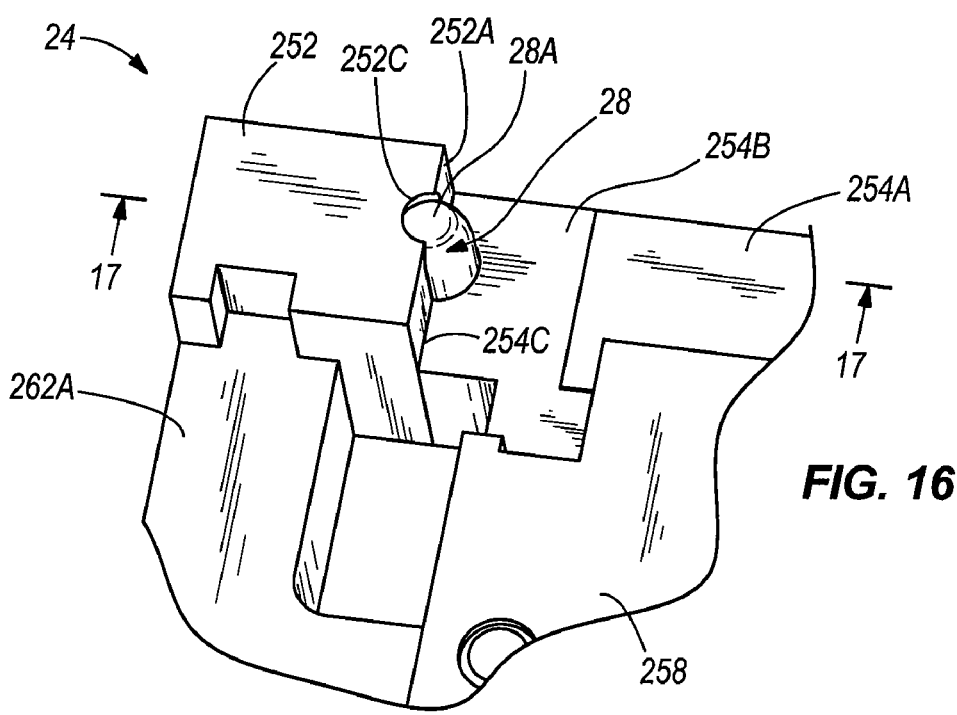
FIG. 16 is an enlarged view of a jaws portion of the capsule holder shown in FIG. 15, the jaws gripping a capsule.
Figure 17:
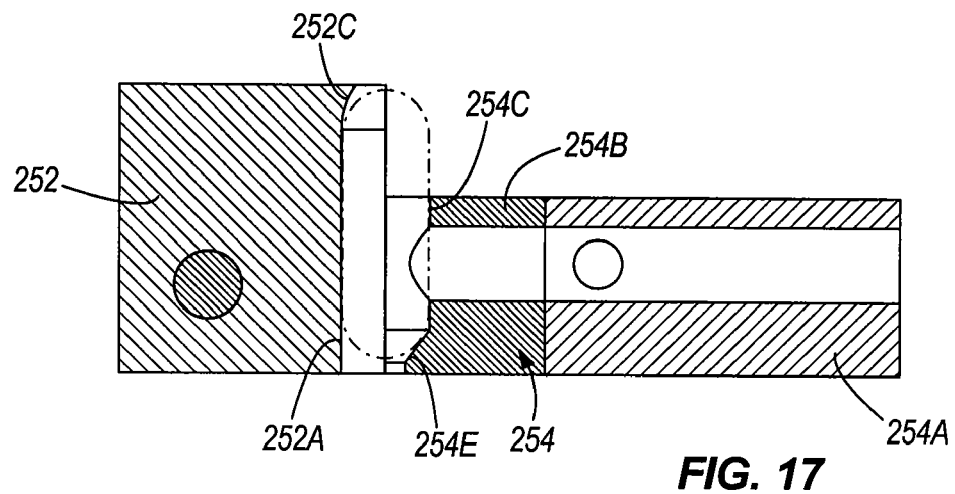
FIG. 17 is a sectional view of the jaws portion of the capsule holder.

FIGS. 1 and 15-17 illustrate the capsule holder 24 according to one embodiment of the invention. The capsule holder 24 supports the capsule 28 during injection of a radiopharmaceutical by the syringe 26. In use, the capsule 28 is manually placed in the capsule holder 24 between two spring-loaded jaws 252, 254 (i.e., a clamp and a support) and after the injection process the capsule 28 is released from the jaws 252, 254 by actuating a release handle 256. The clamp jaw 252 of the capsule holder 24 is spring-loaded and movable between a release position (FIG. 15) and a capture position (FIGS. 16 and 17). The capsule holder 24 includes the clamp 252, the support 254, a base 258, and an actuation system 260. In one embodiment, the clamp 376 and/or the support 380 are formed from a radiation shielding material (e.g., tungsten or coated lead) for providing shielding as the radiopharmaceutical is injected into the capsule 38.

Referring the FIGS. 1 and 15, the base 258 supports the capsule holder 24 and is positioned on the base 78 of the base plate assembly 32 of the capsule preparation system 10. In one embodiment the base 258 may be coupled to the base plate assembly 32. The support 254 includes a mounting bracket 254A and a support plate 254B. A first end of the mounting bracket 254A is coupled to a side surface of the base 258, and a second end of the bracket 254A is coupled to the support plate 254B. The support plate 254B defines an engagement surface 254C having a groove 234D, and the support 254 is positioned such that the engagement surface 254C faces and is aligned with the clamp 252.

The actuation system 260 includes a support arm 262, the clamp 252, the release handle 256, and a spring 264. The support arm 262 is pivotally coupled to a side surface of the base 258. The clamp 252 is coupled to a first end 262A of the support arm 262 by a fastener (not shown), such as a screw or other known fastener. The clamp 252 includes an engagement surface 252A having a groove 252B, and the arm 262 is positioned such that the engagement surface 2526A of the clamp 252 faces and is aligned with the support 254. The spring 264 is positioned between the support arm 262 and the base 258 to bias the clamp 252 to the capture position.

To move the clamp 252 to the release position, the release handle 256 is manually actuated (e.g., by pulling the handle) to move the clamp 252 away from the support by overcoming the bias of the spring 264. The clamp 252 may be held in the release position by continuing to actuate the handle 256; however, once the handle 256 is released, the spring 264 then biases the clamp 252 back to the capture position. The clamp 252 is moved to the release position to position the capsule 28 in the capsule holder 30 and release the capsule 28. The capsule 28 drops into a transport container 266 (schematically illustrated in FIG. 1A) or other container upon release. The transport container may be manufactured from a radiation shielding material, such as lead, tungsten, or the like.

In a further embodiment, the capsule holder drops into a dose calibrator 266 (schematically illustrated in FIG. 1A), which measures the radiopharmaceutical dose or radiation in the capsule. If radioactivity of the dose is greater than a desired radioactivity, the syringe will be set aside and allowed to decay down to a correct dosage. After measurement, the capsule is removed from the dose calibrator and placed in a transport container (not shown). Further, the dose calibrator may be adapted for lifting the capsule to the transport container after measurement occurs.

In a further embodiment, the jaws 252, 254 are actuated by a sensor or switch (e.g., a vision sensor, a solenoid, or the like) to move between the capture and release positions based upon user commands, a sequence of operations, or a sensor.

Referring to FIGS. 16 and 17, the clamp 252 and the support 254 include the engagement surfaces 252A, 254C configured for capturing the capsule 28, including both ends of the capsule. When the clamp 252 is in the capture position, the engagement surfaces 252A, 254C engage each other and the grooves 252B, 254D are aligned. The capsule 28 is positioned within the grooves 252B, 254D. In the illustrated embodiment, the engagement surface 252A of the clamp 252 defines an overlap 252C at a top surface of the clamp 252 and adjacent a first end 28A of the capsule 28. The engagement surface 254D of the support 254 defines an overlap 254E at a bottom surface of the support 254 and adjacent a second end 28B of the capsule 28. Both overlaps 252C, 254E extend partially into the respective groove 252B, 254D, such that when the capsule 28 is captured by the jaws 252, 254, the overlaps 252C, 254E further capture the capsule 38 and prevent the capsule 28 from falling out of the capsule holder 30 during the injection process.

Figure 18:
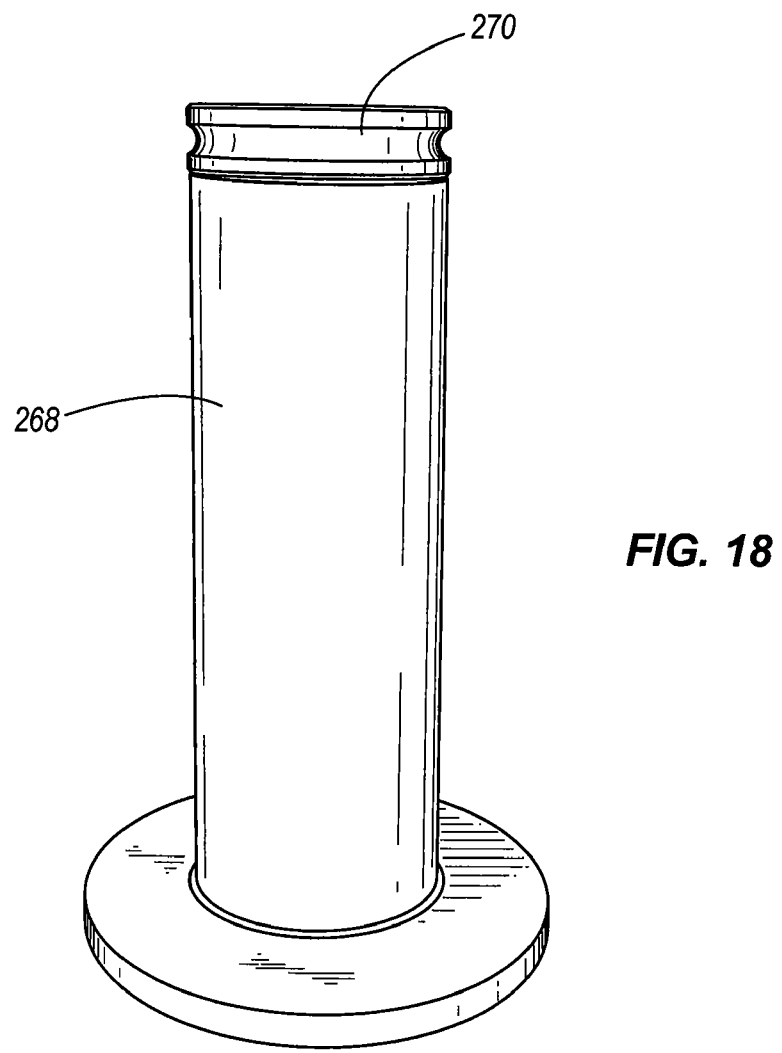
FIG. 18 is a perspective view of a dump container.

FIG. 18 illustrates a dump container 268 for storing damaged syringes. The dump container 268 may be positioned within the housing 30 of the capsule preparation system 10, therefore, if the syringe 25 (e.g., the needle) is damaged during use, the syringe 28 is placed within the container 268 by an operator for later disposal. In one embodiment, the syringe 28 is placed in the container 268 with the forceps 204 shown in FIG. 11. The dump container 268 is formed from a radiation shielding material, such as lead, tungsten, a coated lead material, a tungsten-impregnated material or the like. The container 268 includes a removable cover 270 for permitting access to the container 268 and sealing the damaged syringes within the container 268.

Figure 19:
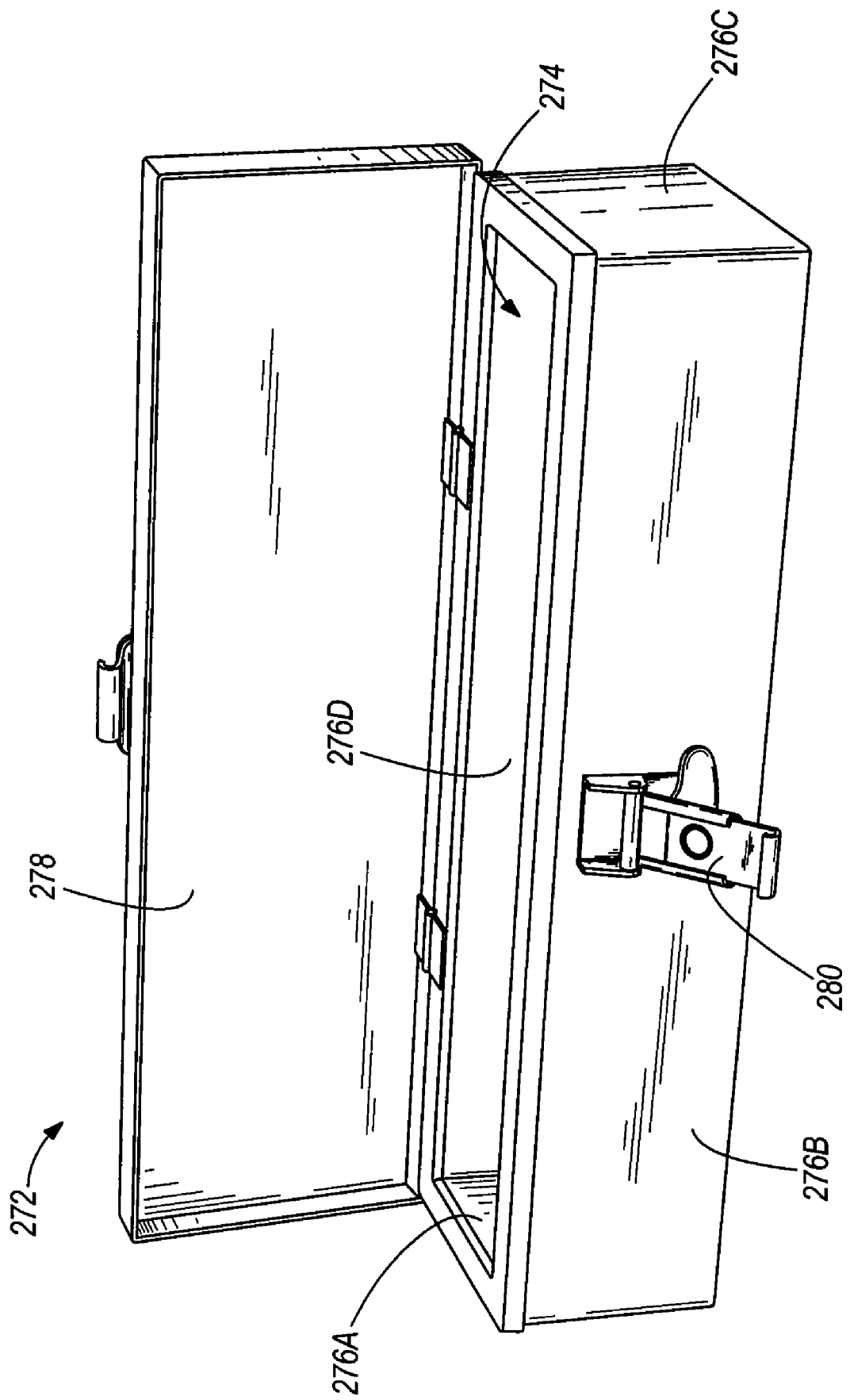
FIG. 19 is a perspective view of a syringe container.

FIG. 19 illustrates a syringe container 272, or coffin, for storing used syringes. The container 272 may be positioned within the housing 30 of the capsule preparation system 10. Once use of a syringe is complete the syringe is deposited in the container 272. The container 272 stores the syringe 28 until decay of lingering radiopharmaceutical occurs. In the illustrated embodiment, the container 272 includes an inner chamber 274 defined by a bottom wall and four side walls 276A-276D, and a cover 278 hingedly coupled to one of the side walls for selectively closing the container 272. The container 272 includes a latch 280, or other known fastener, for securing the cover 278 closed. In one embodiment, the syringe is placed in the container 272 with the forceps 204 shown in FIG. 11. The syringe container 272 is formed from a radiation shielding material, such as lead, tungsten, a coated lead material, a tungsten-impregnated material or the like.

Figure 20:
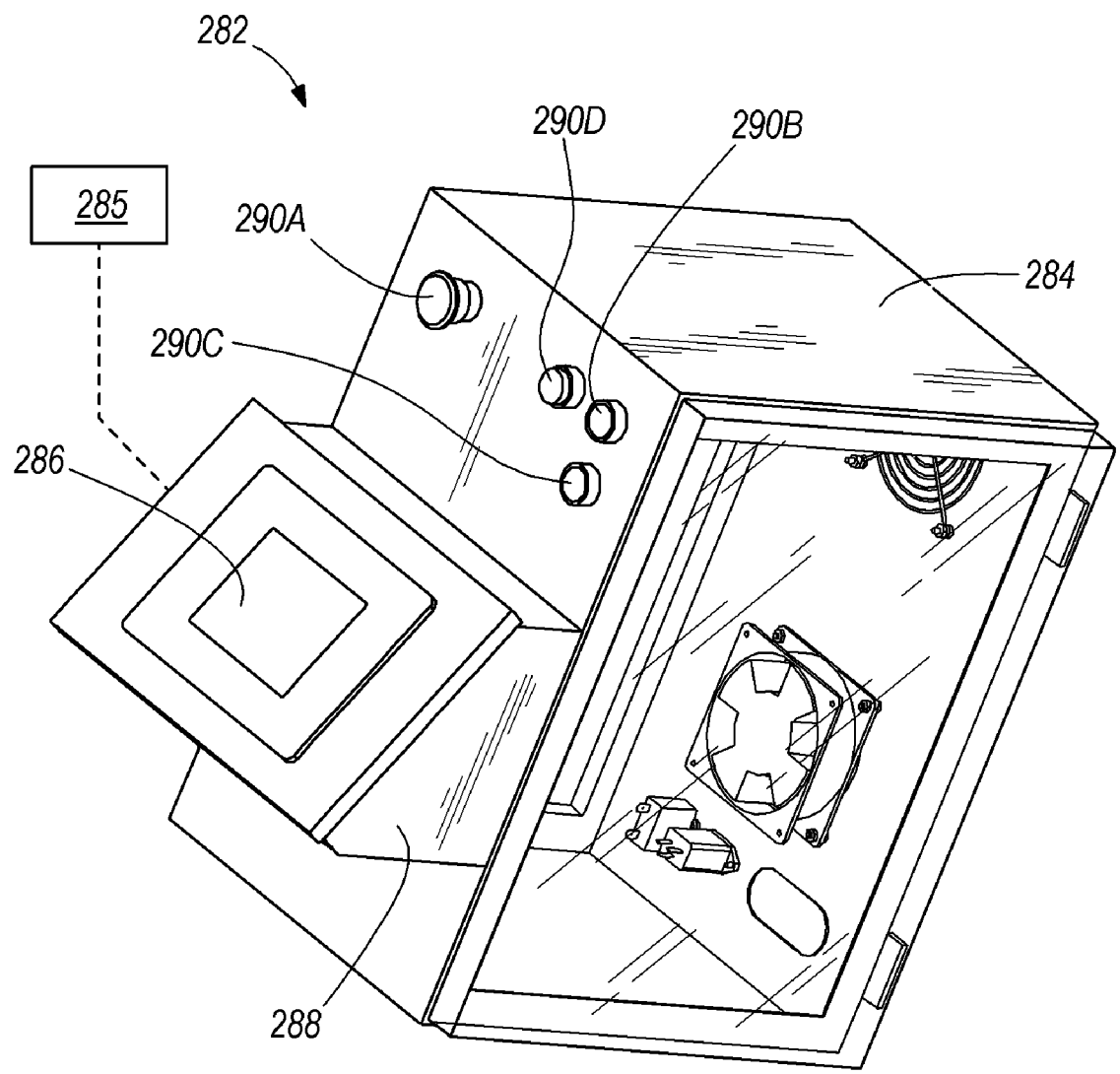
FIG. 20 is a perspective view of a control panel according to one embodiment of the invention.

FIG. 20 illustrates a control panel 282, or user interface, for the capsule preparation system 10 according to one embodiment of the invention. The control panel 282 includes an enclosure 284 for storing a programmable logic controller (PLC), microprocessor, or other known controller 285, which is used to operate the capsule preparation system 10. The control panel 282 may be used to control operations of the capsule preparation system 10 by commands from a software package and/or operator-entered parameters. In the illustrated embodiment, an operator provides commands with a touch panel 286 supported by a console 288. The control panel 282 includes several push-buttons or lights for further controlling the capsule preparation system 10, including an emergency stop button 290A, an on button 290B, an off button 290C, and a power-on light 290D. It should be readily apparent to those of skill in the art that the control panel 282 may include any number of push-buttons or lights directed to a variety of operations.

In one embodiment of the control panel 282, the touch panel 286 may be used to enter the draw volume for the syringe, move the syringe holder system to a safe position, a home position, a needle change position or other position during a capsule preparation process, initiate the capsule preparation process, and provide manager override. Further, the touch panel 286 may be used for commands for a verification process initiated by the controller 285 for the capsule preparation process, or to enter other commands for the system 10, such as inject the plunger (i.e., push the plunger downward) or draw the plunger (i.e., pull the plunger upward). It should be readily apparent to those of skill in the art that the touch panel may be used to enter other operator-initiated actions, verifications or parameters.

The capsule preparation system is 10 operable to draw a radiopharmaceutical from a bulk vial at a desired volume amount and inject the drawn volume of radiopharmaceutical into a capsule. Prior to use of the capsule preparation system 10, the dump container 268 and the syringe container 272 may be placed in the housing of the system 10. The controller 285 positions the syringe holder system 12 in a needle change position (or safe) initiated by operator commands or a software program. In the needle change position, the syringe holder system 12 is positioned at a leftmost end of the first track 114 or opposite the vial holder 16. An operator prepares the syringe 26 with attached needle 26D and installs the syringe 26 in the syringe holder 138. To install the syringe 26, the syringe flange 26C is inserted in the slot 154 of the syringe holder 138 and a free end of the plunger 26A is coupled to the adaptor means 136. Further, the syringe needle 26D is positioned in the groove 164 of the needle holder 140 and between the needle mount 156 and the needle clamp 158. The needle clamp 158 is moved to the clamp position to support the needle 26D within the groove 164 of the needle holder 170.

Before the capsule preparation process can be initiated, the vial is placed in the vial holder 16. In one embodiment, a vial transport container (not shown) is placed in the housing 30 on the second slide 98 of the base plate assembly 32. The transport container is slid along the second slide 98 and positioned adjacent the vial holder 16. An operator transfers the vial to the vial holder 16 with the forceps 204 (FIG. 11). It should be readily apparent to those of skill in the art that the capture portion 226 of the vial capturing device 20 should be in the release position and clear of the vial holder 16 during this step.

After the vial is placed in the vial holder 16, the vial capturing device 20 is moved to the capture position to hold the vial within the vial holder 16. In the capture position, the capture portion 226 of the guide arm 210 contacts an upper lip of the vial and holds the vial within chamber 198 of the vial sleeve 186. In one embodiment, the tube 222 may be positioned within the opening 224 of the guide arm 210 and coupled to the support block 218 after the vial capturing device 20 is moved to the capture position. The charcoal filter (not shown) may also be installed within the tube 222 while the vial capturing device 20 is in the capture position.

Next, the capsule 28 is loaded into the capsule holder 24. In the illustrated embodiment, an operator moves the clamp jaw 252 to the release position by actuating the release handle 256. The clamp jaw 252 is held in the release position while the capsule 28 is positioned between the clamp 252 and the support 380. In the illustrated embodiment, the capsule 38 should be positioned such that one end of the capsule 28 is flush with the overlap 252C of the clamp 252. Once the capsule 28 is properly positioned, the handle 256 is released and the clamp jaw 252 biases back to the capture position to retain the capsule 28 between the clamp 252 and the support 256. It should be readily apparent to those of skill in the art that the capsule 28 may be loaded into the capsule holder 24 before or after the vial is positioned within the vial holder 16.

To initiate a capsule preparation process by the capsule preparation system 10, the controller 285 is turned on at the control panel 282. After the system is turned on, the controller 285 positions the syringe holder system 12 at a home or start position. In the home position, the syringe holder system 12 is positioned at a rightmost limit of the first track 114 and an uppermost limit of the second track 118. Further, in the home position a free end of the syringe needle 26D is positioned within the slot 106A of the needle protection shield 92 to prevent an 4operator from being stuck by the needle.

The operator then selects a desired radiopharmaceutical volume to be drawn and injected for each capsule and initiates the preparation process. In the illustrated embodiment, the system 10 is driven by a volume of radiopharmaceutical in the syringe, although in further embodiments, the system 10 may be driven by a desired radiopharmaceutical dose. In one embodiment, the operator follows a verification process for the capsule preparation system 10 before the preparation process is initiated. Once the preparation process is initiated, operation of the capsule preparation system 10 will begin to draw a radiopharmaceutical dose and fill the capsule. The motor 142 is calibrated such that each turn of the motor equals a set volume of radiopharmaceutical (i.e., mL/step); therefore, the system pulls the desired radiopharmaceutical volume based upon the number of steps taken by the motor. Densities of radiopharmaceutical liquids are generally known and consistent.

The controller 285 moves the syringe 26 to a draw position by moving the syringe holder system 12 from the home position along the first track 114 and the second track 118 such that the syringe needle 26D is positioned directly above the vial and then injected into the vial. The syringe needle 26D is positioned within airspace of the vial and not within the radiopharmaceutical fluid stored in the vial. In one embodiment, the syringe may puncture a vial cap (not shown) before entering the vial. The controller 285 activates the dispensing system 134 to push the plunger 26A into the syringe body 26B to expel air from the syringe body 26B and ensure no air bubble rests on the needle 26D. For example, the dispensing system 134 pushes the plunger 26A downward a distance equal to or greater than upward movement required to draw the radiopharmaceutical volume.

The syringe needle 26D is then inserted into the fluid within the vial by lowering the syringe holder system 14 along the second track 118. The dispensing system 134 then draws a desired radiopharmaceutical volume into the body by pulling the plunger 26A out of the body 26B, i.e., upward. The syringe needle 26D is then repositioned within the airspace of the vial by raising the syringe holder system 12 along the second track 118. To prevent dripping and contamination, the dispensing system 134 pulls the plunger 26A further upward to draw fluid on the needle tip into the syringe 26. The controller 285 then moves the syringe 26 to an inject position by moving the syringe holder system 12 upward along the second track 118 and along the first track 118 such that the syringe needle 26D is positioned directly above the capsule 28 held by the capsule holder 24.

Figure 21:
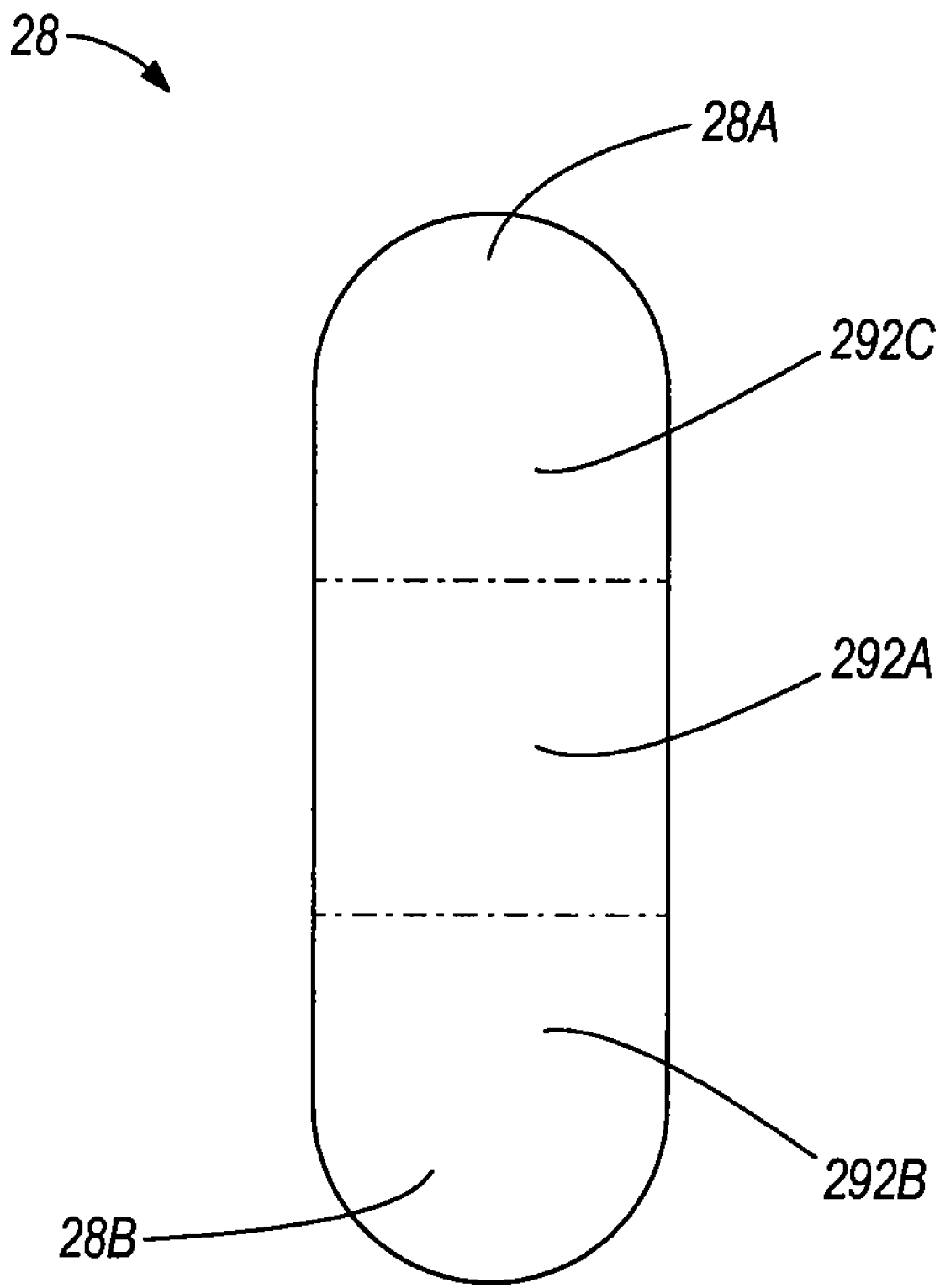
FIG. 21 illustrates one embodiment of a capsule for use with the capsule preparation system.

When certain radiopharmaceuticals (e.g., iodine-131) are dispensed into the capsule 28, the capsule may melt or explode. Therefore, the radiopharmaceutical may be dispensed as the syringe needle 26D is drawn through the capsule 28, which evenly distributes the radiopharmaceutical through the capsule 28. FIG. 21 illustrates one embodiment of a capsule used in the capsule preparation system 10. In the illustrated embodiment, the capsule is a single shell capsule, although in a further embodiment the capsule may be a double shell capsule.

Referring to FIG. 21, the radiopharmaceutical is dispensed within a middle third 292A of the capsule 28. The syringe needle 26D is injected into the capsule 28 by lowering the syringe holder system 12 along the second track 118. Once the needle tip reaches a bottom third 292B of the capsule 28, downward movement of the syringe holder system 12 is stopped. To dispense the radiopharmaceutical, the dispensing system 134 pushes the plunger 26A inward to discharge the radiopharmaceutical from the syringe 26 while the syringe holder system 12 is simultaneously raised upward along the second track 118. Once the needle tip reaches a top third 292C of the capsule 28, radiopharmaceutical should be dispensed from the syringe 26 into the capsule 28 and the plunger 26A pushed completely retracted within the body 26B. The syringe holder system 12 continues moving upward to withdraw the needle 26D from the capsule 28.

The final draw of air into the syringe during the radiopharmaceutical draw portion of the process ensures that the syringe 26 contains a volume of radiopharmaceutical and air. During the dispensing portion of the process, the volume of radiopharmaceutical and air are dispensed into the capsule 28. Thus, the needle and syringe are cleaned of any radiopharmaceutical fluid. In another embodiment, once the syringe needle 26D is withdrawn from the capsule 28, the dispensing system 134 may push the plunger 26A further inward to completely expel radiopharmaceutical from the syringe 26 and the needle tip.

Once the capsule 28 is filled, an operator releases the capsule 28 from the capsule holder 30 by actuating the release handle 256. Actuating the handle 256 moves the clamp jaw 252 to the release position such that the capsule 28 drops into a transport container (not shown). After each capsule filling cycle, the syringe holder system 12 returns to the draw position by the controller 285.

In the illustrated embodiment, an operator initially positions the syringe 26 within the syringe holder 138, places the capsule 28 in the capsule holder 24, sets the unit dose, releases the capsule 28 from the capsule holder 24, and conducts routine change outs of the syringe 26. Otherwise, the capsule preparation process is automated and controlled by the controller 285. During the capsule preparation process the emergency stop button 290A may be pressed to stop operation of the capsule preparation system 10. When power is restored to the system 10, the syringe holder system 12 automatically moves to the home position.

The syringe 26 may be replaced at the end of each dispensing portion of the filling cycle, after a desired number of capsules have been filled, and if the syringe needle 26D is bent. The syringe 26 should not be filled or radioactive during replacement. To remove the syringe 26 from the syringe holder, the controller 285 moves the syringe holder system 12 to the home position, and the needle holder 140 is moved to the release position by pulling the knob 172 to release the needle 26D. In one embodiment, a forceps is used to pull the syringe 26 from the syringe holder 138 and the used syringe is deposited in the syringe container 272. If the syringe 26 needs to be removed because the needle 26D is bent, the syringe 26 is deposited in the dump container 268. If emergency disposal of a syringe is necessary (i.e., while the syringe is filled), the needle 26D is released from the needle holder 170 and the syringe 26 is pulled from the syringe holder 138 for depositing in the dump container 268.

In an embodiment of the capsule preparation system utilizing a stepper motor for the dispensing system 134, the controller 285 uses a correction factor to compensate for compression and expansion of air within the syringe. For each pulse of the motor, the syringe travels a set distance. However, with a syringe there is a compressibility of air within the syringe, therefore, there is no consistent ratio between the motor movement per mL of fluid volume. A linear correction factor is applied to the stepper motor and the motor movement per mL of fluid volume, which provides a consistent ratio between motor movement per mL and repeatability to the preparation process. In one embodiment, the correction factor is based upon elevation and other atmospheric factors at the location of the capsule preparation system.

The constructions and aspects described above and illustrated in the drawings are presented by way of example only and are not intended as a limitation upon the concepts and principles of the present invention. As such, it will be appreciated by one having ordinary skill in the art that various changes in the elements and their configuration and arrangement are possible without departing from the spirit and scope of the present invention. Various features and advantages of the invention are set forth in the following claims.

What is claimed is:

1. A capsule preparation system comprising:
   a syringe holder system for retaining a syringe, the syringe holder system including a support and a syringe holder coupled to the support for receiving the syringe and supporting the syringe relative to the support, the syringe holder system configured for operating a plunger of the syringe;
   a capsule holder for capturing a capsule, the capsule holder configured for selectively releasing the capsule from the capsule holder; and
   a needle holder for supporting a needle of the syringe, the needle holder comprising
   a needle mount coupled to the support and spaced apart from the syringe holder;
   a needle clamp coupled to the support and aligned with the needle mount, the needle clamp movable between a clamp position and a release position,
   wherein at least one of the needle mount and the needle clamp include a groove for receiving the needle, and
   an actuator for moving the needle clamp;
   wherein at least a portion of the syringe holder system, including the syringe holder, is movable along a first direction and a second direction to position the syringe relative to a radiopharmaceutical supply source and the capsule, and the needle holder travels in concert with the syringe holder.

2. The capsule preparation system of claim 1 wherein the first direction is generally horizontal and the second direction is generally vertical.

3. The capsule preparation system of claim 1, and further comprising a controller for controlling operation of the syringe holder.

4. The capsule preparation system of claim 3, and further comprising a user interface configured for an operator to provide input signals to the controller.

5. The capsule preparation system of claim 1 wherein the syringe holder system includes a motor for operating the syringe plunger.

6. The capsule preparation system of claim 1 wherein the syringe holder system further comprises:
a dispensing system for coupling to the syringe plunger, the dispensing system operable to move the plunger relative to a body of the syringe.

7. The capsule preparation system of claim 6 wherein the syringe holder includes a sleeve coupled to the support, the sleeve defining an inner chamber for receiving the plunger and a slot for supporting a flange of the syringe, and further wherein a portion of the dispensing system is received by the inner chamber for coupling to the plunger.

8. The capsule preparation system of claim 6, wherein the dispensing system includes a motor for operating the plunger and an adaptor means for interconnecting the motor and the plunger.

9. The capsule preparation system of claim 1, and further comprising a carrier system for moving the syringe holder along the first direction and the second direction, the carrier system including a first track positioned along the first direction and a second track positioned along the second direction and slidably coupled to the first track, wherein the syringe holder is slidably coupled to the second track.

10. The capsule preparation system of claim 1, and further comprising a vial holder for supporting the supply source, the vial holder formed of a radiation shielding material and including an opening for providing access to the vial by the syringe.

11. The capsule preparation system of claim 10 wherein the vial holder includes a transparent portion.

12. The capsule preparation system of claim 10, and further comprising a support fixture for supporting the vial holder.

13. The capsule preparation system of claim 10, and further comprising a vial capturing device for holding the supply source in position within the vial holder while the syringe draws the radiopharmaceutical dose from the supply source.

14. The capsule preparation system of claim 13 wherein the vial capturing device includes a vent tube having one end for positioning proximate an opening of the supply source.

15. The capsule preparation system of claim 14 wherein the vent tube includes a filter.

16. The capsule preparation system of claim 13 wherein the vial capturing device is selectively movable between a capture position, in which the vial capturing device holds the supply source in position, and a release position.

17. The capsule preparation system of claim 13 wherein the vial capturing device comprises:
a base;
a guide arm movably coupled to the base and defining a capture portion wherein the capture portion holds the supply source in position; and
an actuator for moving the guide arm relative to the base, wherein the actuator moves the guide arm into and out of a capture position.

18. The capsule preparation system of claim 1 wherein the capsule holder includes a pair of spring-loaded grip members for capturing the capsule.

19. The capsule preparation system of claim 18 wherein the capsule holder includes a release handle for separating the grip members.

20. The capsule preparation system of claim 18 wherein the capsule holder includes a solenoid for separating the grip members.

21. The capsule preparation system of claim 1 wherein the capsule holder is formed of radiation shielding material.

22. The capsule preparation system of claim 1, and further comprising a housing for storing the syringe holder and the capsule holder.

23. The capsule preparation system of claim 1, and further comprising a radiation shielding container for storing empty syringes.

24. The capsule preparation system of claim 1, and further comprising a radiation shielding container for storing damaged syringes.

25. A capsule preparation system comprising:
a syringe holder system for retaining a syringe, the syringe holder system configured for operating a plunger of the syringe;
a capsule holder for capturing a capsule, the capsule holder configured for selectively releasing the capsule from the capsule holder;
a vial holder for supporting a radiopharmaceutical supply source, the vial holder formed of a radiation shielding material and including an opening for providing access to the vial by the syringe; and
a vial capturing device for holding the supply source in position within the vial holder while the syringe draws the radiopharmaceutical dose from the supply source, the vial capturing device comprising
a base,
a guide arm movably coupled to the base and defining a capture portion wherein the capture portion holds the supply source in position, and
an actuator for moving the guide arm relative to the base, wherein the actuator moves the guide arm into and out of a capture position;
wherein at least a portion of the syringe holder system is movable along a first direction and a second direction to position the syringe relative to the supply source and the capsule.

* * * * *